(12) United States Patent
Shadnia et al.

(10) Patent No.: US 8,471,073 B2
(45) Date of Patent: *Jun. 25, 2013

(54) ESTROGENIC COMPOUNDS, PROCESS FOR THEIR PRODUCTION AND PHARMACEUTICAL USES THEREOF

(75) Inventors: Hooman Shadnia, Ottawa (CA); James S. Wright, Ottawa (CA); Tony Durst, Ottawa (CA); Muhammad Asim, La Peche (CA)

(73) Assignee: University of Ottawa, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/431,201

(22) Filed: Mar. 27, 2012

(65) Prior Publication Data

US 2012/0190898 A1 Jul. 26, 2012

Related U.S. Application Data

(63) Continuation of application No. 13/091,776, filed on Apr. 21, 2011, now Pat. No. 8,158,684, which is a continuation of application No. 12/365,821, filed on Feb. 4, 2009, now abandoned.

(60) Provisional application No. 61/026,029, filed on Feb. 4, 2008.

(51) Int. Cl.
C07C 39/12 (2006.01)
A61K 31/05 (2006.01)

(52) U.S. Cl.
USPC .......................... 568/734; 514/732

(58) Field of Classification Search
USPC .......................... 568/734; 514/732
See application file for complete search history.

(56) References Cited

U.S. PATENT DOCUMENTS

| | | | |
|---|---|---|---|
| 2,886,589 | A | 5/1959 | Novello |
| 3,686,241 | A | 8/1972 | Amiard et al. |
| 3,707,489 | A | 12/1972 | Teichmuller et al. |
| 4,687,768 | A | 8/1987 | Benedict et al. |
| 4,882,439 | A | 11/1989 | Jones |
| 6,166,075 | A | 12/2000 | Klar et al. |
| 7,074,829 | B2 | 7/2006 | Klar et al. |
| 7,183,445 | B2 | 2/2007 | Jain et al. |
| 2003/0187076 | A1 | 10/2003 | Agoston et al. |

FOREIGN PATENT DOCUMENTS

| | | |
|---|---|---|
| GB | 1140322 | 1/1969 |
| JP | 55-162738 | 12/1980 |
| JP | 08-003091 | 1/1996 |

OTHER PUBLICATIONS

Alberts, Receptor Flexibility in de Novo Ligand Design and Docking, Journal of Medicinal Chemistry, 2005, pp. 6585-6596, vol. 48, No. 21.

Bernstein, The Risk of Breast, Endometrial and Ovarian Cancer in Users of Hormonal Preparations, Basic & Clinical Pharmacology & Toxicology, Jan. 2006, pp. 288-296, vol. 98.
Bolton, Quinoids, quinoid radicals, and phenoxyl radicals formed from estrogens and antiestrogens, Toxicology, 2002, pp. 55-65, vol. 177.
Cavalieri, Initiation of cancer and other diseases by catechol orthoquinones: a unifying mechanism, Cellular and Molecular Life Sciences, 2002, pp. 665-681, vol. 59.
Cavalieri, The Role of Endogenous Catechol Quinones in the initiation of Cancer and Neurodegenerative Diseases, Methods of Enzymology(Quinones and Quinone Enzymes, Part B) 2004, pp. 293-319, vol. 382.
Cavalieri, Catechol estrogen quinones as initiators of breast and other human cancers: Implications for biomarkers of susceptibility and cancer prevention, Biochemica et Biophysica Acta, Reviews on Cancer, 2006, pp. 63-78, vol. 1766, No. 1.
Chen, Synthesis, biological activity and conformational analysis of CD-ring modified *trans*-decalin 1α,25-dihydroxyvitamin D analogs†, Org. Biomol. Chem., 2003, pp. 257-267 vol. 1.
Chichirau, Mechanism of cytotoxicity of catechols and a naphthalenediol in PC12-AC cells: the connection between extracellular autoxidation and molecular electronic structure, Free Radical Biology & Medicine, 2005, pp. 344-355, vol. 38.
Chlebowski, Influence of Estrogen Plus Progestin on Breast Cancer and Mammography in Healthy Postmenopausal Women, 2003, pp. 3243-3253, vol. 289, No. 24.
Deangelis, Indazole Estrogens: Highly selective Ligands for the Estrogen Receptor β Journal of Medicinal Chemistry, 2005, pp. 1132-1144, vol. 48, No. 4.
Flueraru, Cytoxicity and cytoprotective activity in naphthalenediols depends on their tendency to form naphthoquinones, Free Radical Biology & Medicine, 2005, pp. 1368-1377, vol. 39.
Flueraru, Cytotoxicity and Cytoprotective Activity of Naphthalenediols, in Rat Cortical Neurons, American Chemical Society, 2006, pp. 1221-1227, vol. 19, No. 9.
Hauser et al., Synthesis of Some B-Nor-6, 8-secoestranes and B-19-Dinor-6, 8-secopregnanes, Journal of Organic Chemistry, 1978, vol. 43(1), 113-116.

(Continued)

*Primary Examiner* — Sikarl Witherspoon
(74) *Attorney, Agent, or Firm* — Dunlap Codding PC

(57) ABSTRACT

The present invention provides new estrogenic compounds of the general formula

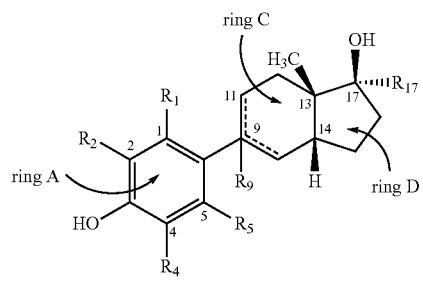

in which the substituents have the meanings that are explained in more detail in the description, and pharmaceutical compositions containing them. The compounds of the invention are useful, for example, in hormone replacement therapies (HRT/ERT) and as contraceptives and estrogenic hormone therapies. Also provided is a process for synthesizing the compounds of the invention.

17 Claims, 3 Drawing Sheets

OTHER PUBLICATIONS

Hussain, Development of Novel Antioxidants: Design, Synthesis, and Reactivity, J. Org. Chem., 2003, pp. 7023-7032, vol. 68, No. 18.

JAMA, Risks and Benefits of Estrogen Plus Progestin in Healthy Postmenopausal Women, American Medical Association, 2002, pp. 321-333, vol. 288, No. 3.

Jordon, Antiestrogens and Selective Estrogen Receptor Modulators as Multifunctional Medicines. 2. Clinical Considerations and New Agents, Journal of Medicinal Chemistry, 2003, pp. 1081-1111, vol. 46, No. 7.

Kahlenborn, Breast Cancer: Its Link to Abortion and Birth Control Pill, One More Soul, 2000.

Kuiper, Comparison of the Ligand Binding Specificity and Transcript Tissue Distribution of Estrogen Receptors α and β, J. Endocrinology 1997, pp. 863-870, vol. 138.

Kuiper, Interaction of Estrogenic Chemicals and Phytoestrogens with Estrogen Receptor β, J. Endocrinology, 1998, pp. 4252-4263, vol. 139.

Liu, Oxidative DNA Damage Induced by Equine Estrogen Metabolites: Role of Estrogen Receptor α, Chem. Res. Toxicol., 2002, pp. 512-519, vol. 15, No. 4.

Liu, Effect of Halogenated Substituents on the Metabolism and Estrogenic Effects of the Equine Estrogen, Equilenin, Chem Res. Toxicol., 2003, pp. 741-749, vol. 16, No. 6.

Obrien, Molecular Mechanisms of Quinone Cytotoxicity, Chem-Biol. Interactions, 1991, pp. 1-41, vol. 80.

Parkin, Cancer Incidence in Five Continents, Oxford University Press, 1997, Fig. 5.1 and Fig. 5.2.

Pezzella, Tyrosinase-Catalyzed Oxidation of 17β-Estradiol: Structure Elucidation of the Products Formed beyond CatecholEstrogen Quinones, Chem. Res.Toxicol., 2005, pp. 1413-1419, vol. 18.

Pratt, Spontaneous retinoic acid receptor β2 expression during mesoderm differentiation of P19 murine embryonal carcinoma cells, Differentiation, 2000, pp. 271-279, vol. 65.

Ruggiero, Estrogen: Physiology, Pharmacology, and Formulations for Replacement Therapy, Journal of Midwifery & Women's Health, 2002, pp. 130-138, vol. 47, No. 3.

Samuni, Semiquinone radical intermediate in catecholic estrogen-mediated cytotoxicity and mutagenesis: Chemoprevention strategies with antioxidants, Proc. Nat. Acad. Sci. 2003, pp. 5390-5395, vol. 100.

Sarabia, Mechanism of Cytochrome P450-Caraly6zed Aromatic Hydroxylation of Estrogens, Chem. Res. Toxicol., 1997, pp. 767-771, vol. 10.

Scaglione, Neurosteroid Analogues. 11. Alternative Ring System Scaffolds: γ-Aminobuturic Acid Receptor Modulation and Anesthetic Actions of Benz[f]indenes, J. Med. Chem., 2006, pp. 4595-4605, vol. 49.

Springer, PostDOCK: A Structural, Empirical Approach to Scoring Protein Ligand Complexes, J. Med. Chem., 2005, pp. 6821-6831, vol. 48.

Warren, A Critical Assessment of Docking Programs and Scoring Functions, J. Med. Chem., 2005, pp. 5912-5931, vol. 49, No. 20.

Wathen, Hormone replacement therapy for the primary prevention of chronic diseases: recommendation statement from the Canadian Task Force on Preventive Health Care, Canadian Medical Assoc. J., 2004, pp. 1535-1539, vol. 170.

Yu, Oxidation of Raloxifene to Quinoids: Potential Toxic Pathways via a Diquinone Methide and o-Quinones, Chem. Res. Toxicol., 2004, pp. 879-888, vol. 17.

Zahid, The Greater Reactivity of Estradiol-3,4-quinone vs Estradiol-2,3-quinone with DNA in the Formation of Depurinating Adducts: Implications for Tumor-Initiating Activity, Chem. Res. Toxicol., 2006, pp. 164-172, vol. 19.

Zhang, The Major Metabolite of Equilin, 4-Hydroxyequilin, Autoxidizes to an o-Quinone Which Isomerizes to the Potent Cytotoxin 4-Hydroxyequilenein-o-quinone, Chem. Res. Toxicol., 1999, pp. 204-213, vol. 12.

Zhao et al., Transformation of Oxidation Products and Reduction of Estrogenic Activity of 17 B-Estradiol by a Heterogeneous Photo-Fenton Reaction, Environmental Science & Technology, 2008, vol. 42(14), 5277-5284.

ESTROGENIC COMPOUNDS, PROCESS FOR THEIR PRODUCTION AND PHARMACEUTICAL USES THEREOF

CROSS-REFERENCE TO RELATED APPLICATIONS

This application is a continuation of U.S. Ser. No. 13/091,776, filed Apr. 21, 2011 now U.S. Pat. No. 8,158,684; which is a continuation of U.S. Ser. No. 12/365,821, filed Feb. 4, 2009, now abandoned; which claims benefit under 35 U.S.C §119(e) of U.S. Provisional Application Ser. No. 61/026,029, filed on Feb. 4, 2008. The entire contents of each of the above-referenced patents and patent applications are expressly incorporated herein by reference.

FIELD OF THE INVENTION

The present invention pertains to the field of estrogenic compounds. More particularly, the present invention pertains to estrogenic compounds that do not readily form quinones in vivo, and to pharmaceutical compositions and methods comprising an estrogenic compound of the invention, or a pharmaceutically acceptable salt, ester or solvate thereof.

BACKGROUND

The safety of long-term steroid usage by women for purposes of estrogen replacement therapy (ERT) or oral contraception (OC) is currently under scrutiny. Epidemiological data can be hard to interpret due to changing patterns of usage and drug formulations. However, based on recent reviews by the WHI and others [1-6], we can at least estimate the magnitude of the problem. Analysis of the increased risk factor for breast cancer for OC users would be about 1.2±0.2, and for ERT users about 1.5±0.2. Using data from the USA, if the median age of OC users is 25 years, the very low rate of cancer incidence in that age group combined with the low risk factor implies very few additional cases per 100,000 women. Given the uncertainty in the risk data and the perceived social benefit, this is generally considered to be a small but acceptable risk [for a different view of OC risk using higher risk factors; however, see ref 7]. For ERT users, their median age of ca. 50 yr has a much higher cancer incidence which, when coupled with the increased risk factor, suggests that there would be about 100-150 additional cases per 100,000 women. This is a significant number of cases, and after review of the epidemiological data, current medical thinking in Canada and the U.S.A. is summarized in a set of recommendations given by the Canadian Task Force on Preventive Health Care in May, 2004 [6]:

Recommendations
1) Given the balance of harms and benefits, the Canadian Task Force on Preventive Health Care recommends against the use of combined estrogen-progestin therapy and estrogen-only therapy for the primary prevention of chronic diseases in menopausal women (grade D recommendation);
2) For women who wish to alleviate menopausal symptoms using hormone replacement therapy (HRT), a discussion between the woman and her physician about the potential benefits and risks of HRT is warranted.

These recommendations raised warning flags for patients and physicians alike, due to the strong demand for hormone replacement coupled with the puzzling risk/benefit analysis implicit in the statement. Of course, a preferable alternative to traditional drugs used as hormone supplements would be a safer, non-carcinogenic compound.

Etiology of Breast Cancer:

The etiology of breast cancer is complex, with hormone-dependent and hormone-independent components [3]. It was originally thought that the only relation between estrogens and cancer was through their ability to stimulate abnormal cell proliferation via estrogen-receptor mediated processes [see ref 8 and references therein]. However, as a result of new evidence on the relationship between estrogens and cancer the field is undergoing a "paradigm shift". A new mechanism of interest, which involves the formation of catechol estrogens as metabolites and their subsequent oxidation to carcinogenic quinones, is not yet considered proven to be the dominant cause of breast cancer, but an increasing amount of evidence in its favor is appearing [8-17].

Quinone Formation and Carcinogenesis:

The naturally occurring estrogens estradiol and estrone have the classic steroid structure containing the A, B, C and D-rings, where estradiol is shown in FIG. 1. The B, C and D rings are saturated, but the A-ring is an aromatic phenol. Phenols are easily metabolized in the liver and elsewhere by the enzyme cytochrome P. 450 hydroxylase [22]. This leads to hydroxyl substitution at the positions adjacent to the first hydroxyl group (situated at position 3 in the A-ring), forming 2-OH estradiol and 4-OH estradiol. These metabolites, termed the "catechol estrogens" [9] can be further metabolized by oxidizing substances present in the cell, e.g. peroxidase/P450 or tyrosinase/$O_2$ [23], or even in the presence of oxygen, to give the 2,3-quinone and the 3,4-quinone [9-17].

Quinones in general are electrophilic compounds which have a tendency to be tumor initiators and promoters, and several such mechanisms are known [22]. They can damage DNA by combining with nucleic acid bases thus causing replication errors [22]. They can deplete essential cellular antioxidants such as glutathione and thiol-containing proteins, subjecting the cell to oxidative stress [22]. They can act directly as free radical generators via reduction to the semi-quinone form and subsequent redox cycling, producing superoxide ion [24]. Different quinones show differing amounts of cytotoxicity due to these competing mechanisms; some, such as the naphthoquinones and anthraquinones are highly cytotoxic [22].

FIG. 1 shows the biological scheme of quinone formation, starting from the natural hormone 17β-estradiol (hereafter "estradiol"). Here the quinone formed involves only the A-ring, i.e., it is a benzoquinone. In the case of one of the conjugated equine estrogens present in the ERT drug Premarin (currently the third most prescribed drug in the USA), the naphthoquinone was formed and it was shown that hamsters treated with the naphthoquinone for 9 months showed 100% tumor incidence [11,12]. This led Bolton, Cavalieri and co-workers to the conclusion that "metabolism of estrogens to catechols and further oxidation to highly reactive o-quinones could play a major role in induction of DNA damage leading to initiation of the carcinogenic process" [8,13,15-17]. This short summary describes the catechol-estrogen hypothesis of the etiology of breast cancer.

ERβ-Selective Agonists:

The recent discovery that estrogens bind similarly to the two receptor subtypes, ERα and ERβ, and that these receptors have different tissue distributions, has resulted in major efforts to develop ligands which are selective agonists for either receptor [32,36 and 37]. Such compounds have considerable potential for the treatment of a number of symptoms and/or diseases associated with estrogen deficiency, including hot flashes, osteoporosis and cardiovascular problems

[37]. Tamoxifen, and raloxifene, although developed before the discovery of the ERβ subtype, are now classified as selective estrogen receptor modulators (SERMs) [32]. Thus, tamoxifen and raloxifene exhibit both estrogenic and anti-estrogenic activity depending on tissue type. The anti-estrogenic activity of both compounds has been exploited to prevent re-occurrence of ER-positive breast cancer and the prevention of breast cancer in high risk women. Both drugs act as an agonist in the bone and thereby help prevent osteoporosis [37]. Tamoxifen, but not raloxifene, also acts as an agonist in the uterus and leads to an increased risk of endometrial cancer. However, neither of these compounds relieves hot flashes, the most common menopausal symptom.

In their search for ERα and ERβ-selective agonists most research groups have targeted non-steroidal families of compounds, inspired by the natural product lead structure genistein. Considerable success has been achieved in this area for structures illustrated, for example, by WAY 202196 and ERB-041 [38 and 39]. These compounds show not only strong binding but also excellent selectivity for ERβ vs. ERα; the binding affinity ERβ/ERα ratios for these structures are: genisten (41); WAY 202196 (78); ERB-041 (226). However, the latter highly ERβ-selective compounds appear to be devoid of classical estrogenic activity. They do not promote the growth of estrogen-dependent MCF-7 breast cancer cells, but also do not relieve hot flashes or protect against osteoporosis. The value of genistein for the treatment of hot flashes has not been unambiguously established, although soy products (containing genistein) are commonly used for this purpose.

There remains a need for estrogenic compounds that avoid the problem of quinone formation, while retaining hormonal activity. Compounds found to have such activity will be useful, for example, in hormone replacement therapy (HRT/ERT), in estrogenic hormone therapies and as contraceptives.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide estrogenic compounds, a process for their production and pharmaceutical uses thereof. In accordance with an aspect of the present invention, there is provided a compound of Formula I, or a pharmaceutically acceptable salt, ester or solvate thereof,

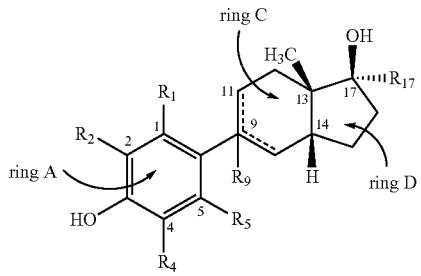

Formula I where
$R_1$ is H, halogen or $CH_3$;
$R_2$ is H, halogen or $CH_3$;
$R_4$ is H, halogen or $CH_3$;
$R_5$ is H, halogen, $CF_3$, $C_1$-$C_5$ alkyl, $CH_2OH$, $CH_2OAc$, $CH_2CH_2OH$, $CH_2CH_2OAc$, $CH_2$-aryl, $CH_2$-heteroaryl, $CH=CH_2$, $CH_2CH_2SCH_3$, $CH_2CH_2SC_2H_5$, $CH_2CH_2SCH_2Ar$, $CH_2CH_2SCH_2$-heteroaryl, OH, $OCH_3$, $OC_2H_5$, $OCH_2Ar$, $OCH_2$-heteroaryl, OAc, $SCH_3$, $SC_2H_5$, $SCH_2Ar$, $SCH_2$-heteroaryl, $SOCH_3$, $SOC_2H_5$, $SOCH_2Ar$, $SOCH_2$-heteroaryl, $SO_2CH_3$, $SO_2C_2H_5$, $SO_2CH_2Ar$, $SO_2CH_2$-heteroaryl, CN, CHO, $COCH_3$, $COC_2H_5$, $CO_2H$, $CO_2CH_3$, $CO_2C_2H_5$, $CO_2CH_2Ar$, $CO_2CH_2$-heteroaryl, $CONH_2$, $CON(CH_3)_2$, $CON(CH_2)_4$, $CON(CH_2)_5$; $NO_2$
$R_9$ is absent, H or OH
$R_{17}$ is H or $C_2H$.

Preferably, the compound of Formula I has the following structure of Formula Ia:

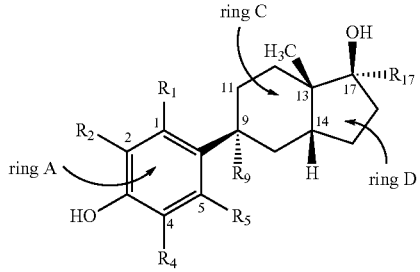

Formula Ia

In accordance with another aspect of the invention, there is provided a composition comprising a compound of Formula I, or a pharmaceutically acceptable salt, ester or solvate thereof, and a pharmaceutically acceptable diluent or excipient.

In accordance with another aspect of the invention, there is provided a method of hormone replacement therapy comprising administering a compound of Formula I, or a pharmaceutically acceptable salt, ester or solvate thereof, to a subject in need thereof In accordance with another aspect of the invention, there is provided a method of oral contraception comprising administering a compound of Formula I, or a pharmaceutically acceptable salt, ester or solvate thereof, to a subject.

In accordance with another aspect of the invention, there is provided a method of estrogenic hormone therapy comprising administering a compound of Formula I, or a pharmaceutically acceptable salt, ester or solvate thereof, to a subject in need thereof In accordance with another aspect of the invention, there is provided a process for synthesizing a compound of Formula I, comprising coupling an enantiomerically pure ketone of Formula II with a lithium compound of Formula III,

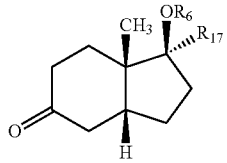

Formula II

-continued

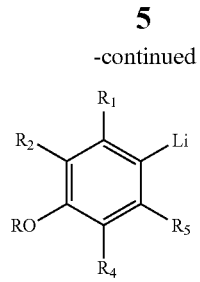

Formula III where R and $R_6$ are independently H, alkyl or a protecting group and $R_1$, $R_2$, $R_4$, $R_5$ and $R_{17}$ have the meaning defined above in relation to Formula I.

DETAILED DESCRIPTION OF THE INVENTION

Figure 1:
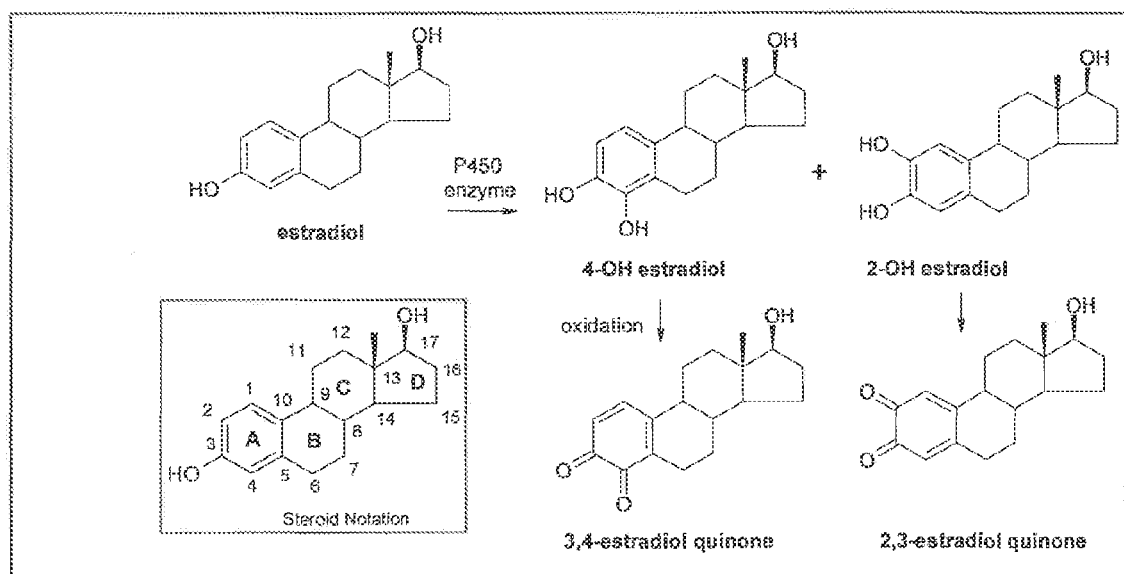
FIG. 1 is a schematic of the hydroxylation of estradiol to form the catechol estrogens 2-OH estradiol and 4-OH estradiol, followed by their (auto)oxidation to form the corresponding 2,3- and 3,4-quinones.

Unless defined otherwise, all technical and scientific terms used herein have the same meaning as commonly understood by one of ordinary skill in the art to which this invention belongs.

The present invention provides estrogenic compounds that avoid or minimize the problem of quinone formation, which is typically associated with compounds currently used in ERT. The compounds of the invention have the structure of Formula I, or are pharmaceutically acceptable salts, esters or solvates thereof,

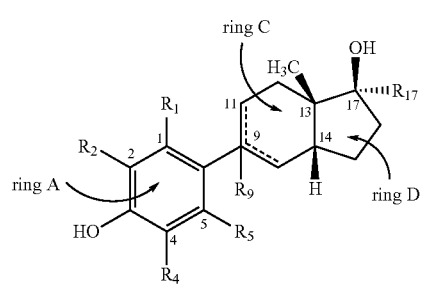

Formula I where
$R_1$ is H, halogen or $CH_3$;
$R_2$ is H, halogen or $CH_3$;
$R_4$ is H, halogen or $CH_3$;
$R_5$ is H, halogen, $CF_3$, alkyl, $CH_2OH$, $CH_2OAc$, $CH_2CH_2OH$, $CH_2CH_2OAc$, $CH_2$-aryl, $CH_2$-heteroaryl, $CH=CH_2$, $CH_2CH_2SCH_3$, $CH_2CH_2SC_2H_5$, $CH_2CH_2SCH_2Ar$, $CH_2CH_2SCH_2$-heteroaryl, OH, $OCH_3$, $OC_2H_5$, $OCH_2Ar$, $OCH_2$-heteroaryl, OAc, $SCH_3$, $SC_2H_5$, $SCH_2Ar$, $SCH_2$-heteroaryl, $SOCH_3$, $SOC_2H_5$, $SOCH_2Ar$, $SOCH_2$-heteroaryl, $SO_2CH_3$, $SO_2C_2H_5$, $SO_2CH_2Ar$, $SO_2CH_2$-heteroaryl, CN, CHO, $COCH_3$, $COC_2H_5$, $CO_2H$, $CO_2CH_3$, $CO_2C_2H_5$, $CO_2CH_2Ar$, $CO_2CH_2$-heteroaryl, $CONH_2$, $CON(CH_3)_2$, $CON(CH_2)_4$, $CON(CH_2)_5$; $NO_2$;
$R_9$ is absent, H or OH; and
$R_{17}$ is H or ethynyl (i.e., CCH).

As would be readily appreciated by a skilled worker, the solvate can be a hydrate.

It should also be noted that if the stereochemistry of a structure or a portion of a structure is not indicated with, for example, bold or dashed lines, the structure or the portion of the structure is to be interpreted as encompassing all stereoisomers of it. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

As used herein, the term "alkyl" is used to refer to a straight or branched chain hydrocarbon having from 1 to 5 carbon atoms. The term "alkyl" includes saturated hydrocarbons as well as alkenyl and alkynyl moieties.

As used herein, the term "aryl" is used to refer to an aromatic hydrocarbon group containing 6 to 10 carbon atoms.

As used herein, the term "halogen" is used to refer to fluorine, a chlorine, a bromine or an iodine. A preferred example of such a halogen is a fluorine or chlorine.

As used herein, the term "heteroaryl" is used to refer to a 5- or 10-membered aromatic heterocyclic group containing one or more heteroatoms selected from an oxygen atom, a nitrogen atom, and a sulfur atom.

Preferably, the compound of Formula I has the following structure and stereochemistry:

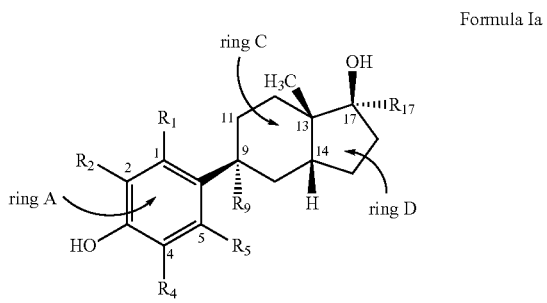

Formula Ia wherein, $R_1$, $R_2$, $R_4$, $R_5$, $R_{17}$ are as defined above, and $R_9$ is H or OH.

In accordance with a specific embodiment of the present invention there is provided a compound having a structure of Formula I, or a pharmaceutically acceptable salt, ester or solvate thereof, wherein
$R_1$ is H, F or $CH_3$;
$R_2$ is H or F;
$R_4$ is H or F;
$R_5$ is H, F, Cl, $CF_3$, $CH_3$, $C_2H_5$, $nC_3H_7$, $iC_3H_7$, $CH_2OH$, $CH_2OAc$, $CH_2CH_2OH$, $CH_2CH_2OAc$, $CH_2$-aryl, $CH_2$-heteroaryl, $CH=CH_2$, $CH_2CH_2SCH_3$, $CH_2CH_2SC_2H_5$, $CH_2CH_2SCH_2Ar$, $CH_2CH_2SCH_2$-heteroaryl, OH, $OCH_3$, $OC_2H_5$, $OCH_2Ar$, $OCH_2$-heteroaryl, OAc, $SCH_3$, $SC_2H_5$, $SCH_2Ar$, $SCH_2$-heteroaryl, $SOCH_3$, $SOC_2H_5$, $SOCH_2Ar$, $SOCH_2$-heteroaryl, $SO_2CH_3$, $SO_2C_2H_5$, $SO_2CH_2Ar$, $SO_2CH_2$-heteroaryl, CN, CHO, $COCH_3$ $COC_2H_5$, $CO_2H$, $CO_2CH_3$, $CO_2C_2H_5$, $CO_2CH_2Ar$, $CO_2CH_2$-heteroaryl, $CONH_2$, $CON(CH_3)_2$, $CON(CH_2)_4$, $CON(CH_2)_5$; $NO_2$, $R_9$ is H or OH; and $R_{17}$ is H or ethynyl.

Preferably, $R_5$ is H, F, Cl or $CH_3$.

Figure 3:
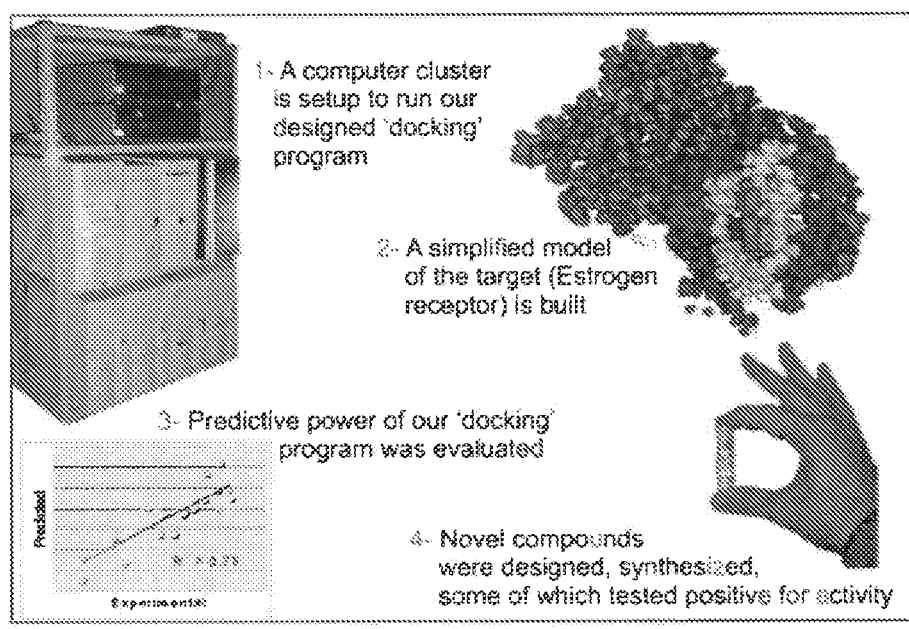
FIG. 3 provides a schematic overview of drug design implementation used in the invention. 1) a computer cluster used for computational analysis, 2) a model of estrogen receptor showing test ligand (blue) inside first amino acid envelope, 3) correlation of RBA predicted vs. experimental from docking program, 4) synthesis of novel compounds to be tested for Relative Binding Affinity (RBA). Not shown: Additional tests for hormonal potency, acute and long-term toxicity.

In designing the compounds of the present invention, a multi-step process was employed. First a preliminary screen was performed on a computer using a program that facilitates the visualization of ligand-receptor interface, where the receptor in this case is an estrogen receptor. This initial pre-screen was done to identify candidate compounds suitable for further computational analysis. A second computer-implemented screen was performed using a docking algorithm that provides a predicted relative binding affinity (RBA) for each compound. This second screen was performed to identify a series of high affinity lead compounds. Finally, the lead compounds were synthesized and tested as described below. The overall process is depicted in FIG. 3.

Computational Drug Design

Molecular Operating Environment computing platform [MOE, 2008] was selected for drug design. This software is developed by the Chemical Computing Group (CCG) in Montreal and is attracting increased international usage. PC Spartan was used to calculate ligand solvation energies [29]. A validation study was performed on a set of 25 ligands known to bind to human recombinant ERα [11-13, 30, 31]. First, a computer cluster (FIG. 3-1) was set up to handle the extensive computational requirements associated with conformational freedom of ligands and receptor flexibility [25, 26]. Modifications to existing software were required to make such a study feasible, and a "shell model" of the receptor protein was created (FIG. 3-2) which made study of ligand-receptor interactions much faster, e.g., a total CPU time of about 1 day per molecule. Techniques were also introduced to allow the protein geometry to relax to accommodate the ligand and tested various "scoring functions" to rank ligand poses; the latter were compared to the log of the experimental RBA. Optimization of the training set and scoring function was performed and produced a strong correlation (FIG. 3-3), which allowed prediction of novel "agonists" that would obey the design criteria.

Figure 2:
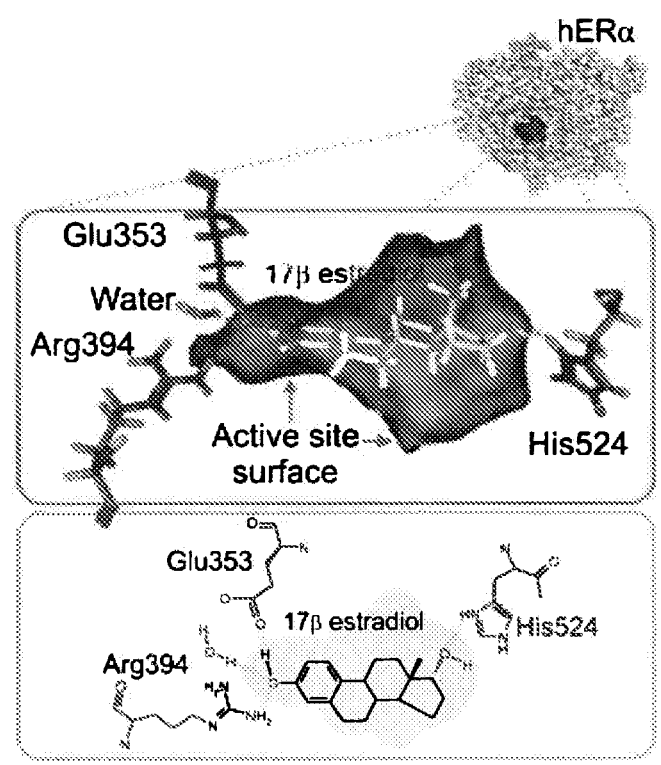
FIG. 2 depicts ligand-receptor interaction for estradiol in 2D and 3D representations. The important H-bond networks at positions 3 and 17 are shown.

In addition to the above development of the docking algorithm, recent improvements in visualization of the ligand-receptor interface were made by Chemical Computing Corporation which helped in establishing the preliminary screen for optimal ligand binding. Briefly, the H-bonding network which is optimum for estradiol was assumed to be important; this provides H-bond anchors at receptor residues Glu353, Arg394 and His524 (FIG. 2). As in estradiol a water molecule was retained in the receptor cavity, which should participate in the H-bonding (FIG. 2). To optimize the H-bond network the O—O distance should be near 11 A, as in estradiol. Next, using FIG. 2 to visualize the receptor cavity, the ligand should not cross the boundary of the cavity excessively, or the protein will be unable to adjust sufficiently to accommodate it. Finally, the solvation energy of the ligand (computed using PC Spartan software [28]) must not be too large since the ligand must be de-solvated when entering the receptor. Constraints on the ligand described above are similar to a "pharmacophore model" discussed by John Katzenellenbogen and coworkers [33] and used as a screening technique prior to their own syntheses.

Using the criteria above as a pre-screen requires only about 5 minutes and allows rejection of many otherwise apparently promising compounds. Molecules which passed the pre-screening tests were sent to the docking program described above and an RBA for each compound was predicted for binding to ERα. A series of predicted high-affinity lead compounds were synthesized and tested as set out below.

Synthesis of Compounds

In accordance with another aspect of the invention, there is provided a process for synthesizing a compound of Formula I, comprising coupling an enantiomerically pure ketone of Formula II with a lithium compound of Formula III,

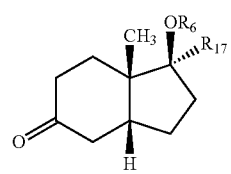

Formula II

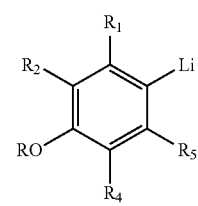

Formula III where R and $R_6$ are independently H, alkyl or a protecting group and $R_1$, $R_2$, $R_4$, $R_5$ and $R_{17}$ have the meaning defined above in relation to Formula I. As described in more detail below, the lithium compound of Formula III can be prepared using known techniques, for example, by reacting the corresponding brominated compound nBuLi. The product of the coupling reaction is a mixture of unsaturated hydroxyl isomers, which are subsequently subjected to dehydrogenolysis and deprotection (as necessary) and the resultant isomers are separated to yield the compound of Formula I.

As would be readily appreciated by a worker skilled in the art, alternative synthetic methods can be used to prepare the compounds of the present invention.

In describing the compounds of the invention, it is important to note that their numbering is based on steroid numbering, as shown below.

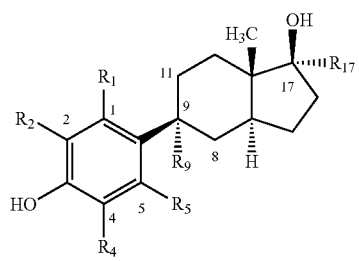

ACD-estrogen

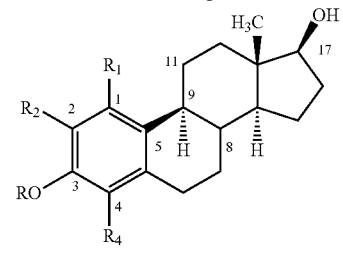

estradiol

Compound 1, the first target molecule, was synthesized and studied by radiolabel assay to determine binding activity. Relative to estradiol (set at 100%) the RBAs for ERα and ERβ were determined to be 1.5% and 21.5%, respectively. This demonstrated that ring A can be successfully coupled to rings CD and that the first such compound shows selective binding, favouring ERβ by a factor of 15. However, it was found not to block formation of quinones.

Activity Testing

The compounds of the present invention are estrogenic and do not readily metabolize to quinones in vivo. Following synthesis, the compounds were tested to confirm their properties are as predicted by the computational analyses described above.

Tests for Relative Binding Affinity:

These tests are well described in the literature [31]. Briefly, a radiolabel assay is used where competition for the receptor binding site is set up between radiolabeled estradiol and the ligand under investigation. Displacement of the radioactivity means that the ligand shows binding to the receptor, and this is quantified to give the relative binding affinity (RBA). Here strong binding is highly correlated with hormonal potency (unless antagonists are designed deliberately, which was not the goal of the present invention).

mRNA Transcription Assay:

This assay, which is a measure of hormonal potency, is also given in the literature and follows standard protocols [12]. For hormone assays an estrogen response element driven luciferase will be transfected into COS-7 ER+ cells, to test for transcriptional activation by test compounds relative to estradiol. Compounds with estrogenic activity cause luciferase production, which is monitored by luminescence detection using standard well-known techniques.

Quinone Related Toxicity Assay:

The toxicity of test compounds is determined by exposure of intact hepatocytes to the test compound. Toxicity levels are expressed as LC50 values following 2 hour exposure.

Tests for Carcinogenicity:

The protocol used in Pratt's laboratory on studies of retinoic acid and its receptor [35] will be used to test the compounds of the present invention. MCF-10A cells will be used, which are immortalized human mammary epithelial cells devoid of tumorigenic activity. These cells will be subjected to parent drug or metabolites at increasing concentrations for periods between 5 and 25 days. Cells will then be trypsinized and replated in soft agar at the end of the treatment period and assessed for anchorage-independent colony formation. Some cells will continue to be exposed to drug by inclusion of the appropriate concentration to determine tumor promoter activity, while others will remain without. Colonies will be isolated and expanded. Incidence of mutation will be determined using the HPRT gene as an indicator by growth in 6-thioguanine. Commonly upregulated genes, including c-myc, p65 Rel-A, survivin, p53(mut) and PIN 1, will be assessed by immunoblot and RT-PCR. Transforming quinones, i.e., 4-OH equilenin, will be compared with the novel compound and its metabolites in the MCF-10A transformation assay.

To assess tumorigenicity, ca. $1 \times 10^6$ cells from 20 different colonies will be injected subcutaneously into 8 week-old female nude mice. These mice are sexually mature and produce normal levels of endogenous estrogen. Mice will be examined on a weekly basis for tumor formation over a period of 1 year. Tumors will be measured and weighed after sacrifice and parameters including ER/PR status and mitotic index assessed. The results will permit comparison of the inherent tumorigenic activity of estradiol to that of the compounds of the invention. To be pharmaceutically useful, compounds should exhibit low or zero tumorigenicity.

Pharmaceutical Compositions and Uses Thereof

The compounds of the present invention are useful as estrogenic compounds. One aspect of the invention provides methods for treating or preventing disorders related to estrogen functioning. For example, the compounds of the present invention can be administered as alternatives to current hormone/estrogen replacement therapies (HRT/ERT), estrogenic hormone therapies and oral contraceptives. Accordingly, one aspect of the invention provides a method of hormone replacement therapy comprising administering a compound of Formula I, or a pharmaceutically acceptable salt, ester or solvate thereof, to a subject in need thereof. Another aspect of the invention provides a method of oral contraception comprising administering a compound of Formula I, or a pharmaceutically acceptable salt, ester or solvate thereof, to a subject.

In another example, the present invention provides a method of estrogenic hormone therapy (EHT) comprising administering a compound of Formula I, or a pharmaceutically acceptable salt, ester or solvate thereof, to a subject in need thereof. EHT is a general term used to refer to a broad range of indications including, but not limited to, female hypogonadism, osteoporosis, castration, primary ovarian failure, amenorrhea, dysmenorrhea, oligomenorrhea, lactation suppression, growth attenuation, and some male infertility or prostate cancer treatments.

The term "subject" as used herein, refers to an animal, preferably a mammal, most preferably a human, who has been, is or will be the object of treatment, observation or experiment.

Administration of the compound of the present invention can be carried out via any of the accepted modes of administration or agents for serving similar utilities. Thus, administration can be, for example, orally, nasally, parenterally, topically, transdermally, or rectally, sublingually, intramuscular, subcutaneously, or intravenously in the form of solid, semi-solid, lyophilized powder, or liquid dosage forms, such as for example, tablets, suppositories, pills, soft elastic and hard gelatin capsules, powders, solutions, suspensions, or aerosols, or the like, preferably in unit dosage forms suitable for simple administration of precise dosages. The compositions will include a conventional pharmaceutical carrier or excipient and a compound of the present invention as the/an active agent, and, in addition, may include other medicinal agents, pharmaceutical agents, carriers, adjuvants, etc.

In accordance with specific embodiments of the invention, such compositions will take the form of a capsule, caplet or tablet and therefore optionally also contain a diluent, a disintegrant, a lubricant and/or a binder.

Alternatively, a compound of the invention can be formulated into a suppository using, for example, about 0.5% to about 50% active ingredient disposed in a carrier that slowly dissolves within the body, e.g., polyoxyethylene glycols and polyethylene glycols (PEG), e.g., PEG 1000 (96%) and PEG 4000 (4%), and propylene glycol.

Liquid pharmaceutically administrable compositions can, for example, be prepared by dissolving, dispersing, etc., a compound of the invention (e.g., about 0.5% to about 20%), and optional pharmaceutical adjuvants in a carrier, such as, but not limited to, water, saline, aqueous dextrose, aqueous cyclodextrin, glycerol, ethanol or the like, to thereby form a solution or suspension.

If desired, a pharmaceutical composition of the invention can also contain minor amounts of auxiliary substances such as wetting or emulsifying agents, pH buffering agents, antioxidants, and the like.

Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention.

The therapeutically effective amount of a compound of the invention will vary depending upon a variety of factors including the age, body weight, general health, diet, mode and time of administration, rate of excretion, drug combination, the severity of the particular disease-states, and the host undergoing therapy.

The above paragraphs all apply to use of the compounds for monotherapy applications, i.e., where only one compound at a time is used. However, the RBAs of the developed compounds show a range of binding affinities ranging from strongly ERα-selective to strongly ER-β selective. It can be desirable to use a mixture of both types of compounds as a combination therapy.

To gain a better understanding of the invention described herein, the following examples are set forth. It should be understood that these examples are for illustrative purposes only. Therefore, they should not limit the scope of this invention in any way.

EXAMPLES

Example 1

Synthesis of ACD Estrogenic Compounds

Scheme 1 outlines a general scheme useful for the synthesis of the ACD ring-containing compounds of the present invention.

The CD ring moiety, compound 3, was synthesized in enantiomerically pure form following an established literature procedure.

The A ring part, compound 1, was either obtained from a commercial source as the corresponding phenol or was synthesized via known literature methods that typically involved purchasing the non-brominated precursor and then carrying out an electrophilic bromination using either $Br_2$ or N-bromosuccinimide in a suitable solvent.

The phenolic OH and the secondary OH in the D ring were protected (to —OR or —$OR_6$, respectively) in order to be non-reactive to the n-Butyllithium (BuLi) treatment by conversion to ethers using groups such as $CH_3$—, $PhCH_2$—$CH_2$=CH—$CH_2$, $CH_3OCH_2$-[MOM], or tetrahydropyranyl, [THP] or conversion to silyl ethers such as tertbutyldimethylsilyl (tBDMS). Subsequent deprotection was performed using known methods for deprotection. R and $R_6$ can be the same or different protecting groups.

Alternatively, the phenolic OH is not protected and the reaction was performed using an extra equivalent of nBuLi instead.

Furthermore, if the substituents on the A ring are reactive to nBuLi, then it can be necessary to include additional steps for protection (and subsequent deprotection) of these substituents. Again, the protection and deprotection steps were performed using standard methods.

Commercial nBuLi in tetrahydrofuran (THF) was used most commonly to convert compound 2 into the nucleophilic lithiated derivative. Alternatively the magnesium derivative can be prepared using either Mg in ether or THF or isopropyl magnesium chloride in THF as the reagent to carry out the bromine to metal exchange. The halogen metal exchange reaction can also be carried out on the iodo analogs of compound 2 and in some cases on the chloro analogs of compound 2.

Compound 4 is obtained as a mixture of isomers that can, but need not be separated. Each is easily dehydrated to give a mixture of the unsaturated isomers 5 and 6. This mixture shows good binding to the estrogen receptors. The sequence 4 to 7 can be carried out in a single pot with aqueous acid. For the purpose of preparing the desired compound 7, the mixtures of alkenes 5 and 6 were not separated but hydrogenated with $H_2$/Pd/C which leads to a separable mixture of 7 and 8. These were separated via silica gel column chromatography. There are many other known hydrogenation catalysts that could have been used in place of Pd/C.

Compounds 4 can also be formed from 2 and 3 without protecting the hydroxyl group of 3. In such cases two equivalents of 2 and slightly more than 2 equivalents of BuLi was used per equivalent of compound 3.

The structures were assigned on the basis of their proton and carbon NMR spectra. The beta isomers 6 have the natural steroid stereochemistry. These compounds bind most strongly to the estrogen receptors. They show ERβ to ERα selectivity that is typically greater than 5:1.

The sequence of reactions from compound 4 to 7, that is dehydration, deprotection and hydrogenation can be changed. The choice is dictated by the properties the various intermediates and the ease of separation. One possible example is dehydrogenation, hydrogenation, separation of the isomers at C9 and then deprotection.

The triethylsilane induced hydrogenolysis of the C9 hydroxyl group can also be carried out after deprotection steps that do not cause dehydration. Other known methods of hydrogenolysis of the C9 hydroxyl group in compound 4 or a deprotected version thereof, such as Raney Nickel/ethanol or via acid catalyzed $NaBH_3CN$ can also be used.

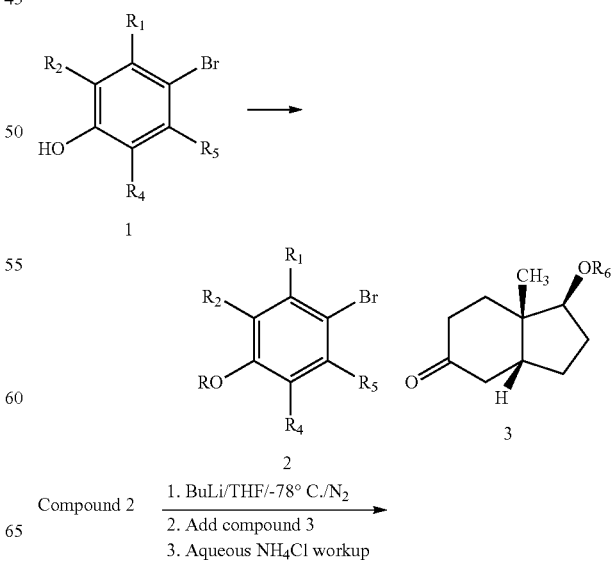

Scheme 1

-continued

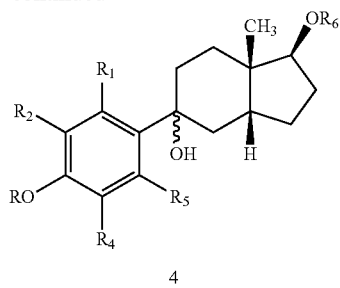

4

Compound 4 →(dehdrate and deprotect)

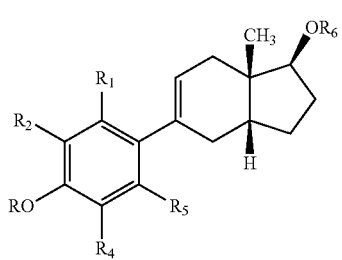

5

+

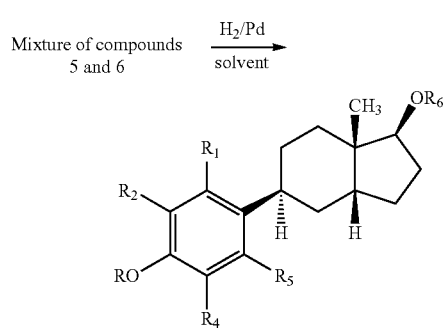

6

Mixture of compounds 5 and 6 →(H₂/Pd, solvent)

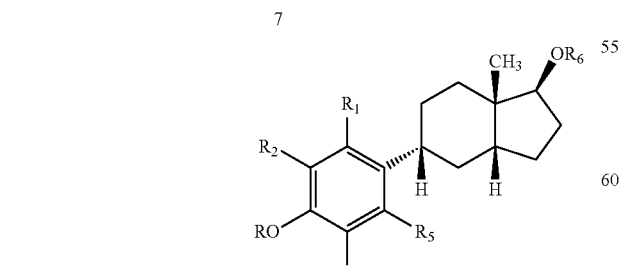

7

+

8

Example 2

Synthesis of ACD Estrogenic Compounds via Alternate Route 1

Scheme 2 depicts an alternative route for the synthesis of compounds of Formula I in which there is a double bond at C11-C9 or C9-C8.

Scheme 2

Compound 3 →($Tf_2O$, $R_3N$,/$CH_2Cl_2$)

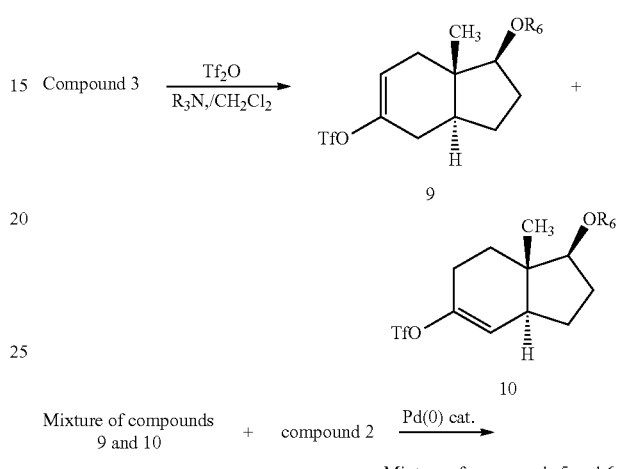

9

+

10

Mixture of compounds 9 and 10 + compound 2 →(Pd(0) cat.) Mixture of compounds 5 and 6

Example 3

Synthesis of ACD Estrogenic Compounds via Alternate Route 2

Scheme 3 generally depicts a method for resolving the racemic compound 4 into its enantiomers.

Scheme 3

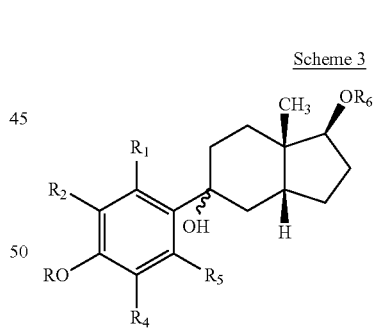 →($BF_3Et_2O$/$Et_3SiH$, $CH_2Cl_2$) 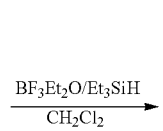

4

Mixture of compounds 7 and 8

Example 4

Experimental Procedures for Synthesis of ACD Estrogenic Compounds

General

All moisture sensitive reactions were carried out under nitrogen atmosphere. Anhydrous solvents were obtained as follows: THF, Et₂O, distilled from sodium and benzophenone; CH$_2$Cl$_2$ distilled from CaH$_2$. Analytical TLC was performed with 0.25 mm silica gel 60F plates with 254 nm fluorescent indicator from Merck. Plates were visualized by ultraviolet light and treatment with acidic ceric ammonium nitrate or potassium permanganate stains followed by gently heating. Silica gel 60, (40-60 um) was purchased from Aldrich. The $^1$HNMR and $^{13}$C NMR was recorded on a Bruker Avance 500, 400 and 300 spectometer. Mass spectroscopy (MS), using either electron impact (EI) or chemical ionization (CI), was performed on a V. G. Micromass 7070 HS mass spectrometer with an electron beam energy of 70 eV (for EI). High-resolution mass spectroscopy (HRMS) was performed on a Kratos Concept-11A mass spectrometer with an electron beam of 70 eV, or a JEOL double focusing magnetic sector mass spectrometer JMS-AX505H.

General Procedures:

Synthesis of CD Ring Moiety 3. (Hajos-Parrish Ketone)

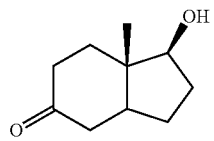

This compound was prepared in enantiomerically pure form following the very well known Hajos-Parrish ketone procedures. a) Hajos, Z. G.; Parrish, D. R. *Org. Synth.* 1984, 63, 26; b) Micheli, R. A.; Hajos, Z. G.; Cohen, N.; Parrish, D. R.; Portland, L. A.; Sciamanna, W.; Scott, M. A.; Wehrli, P. A. *J. Org. Chem.* 1975, 40, 675.

Protection of the Bromophenols as TBDMS Ethers 1:

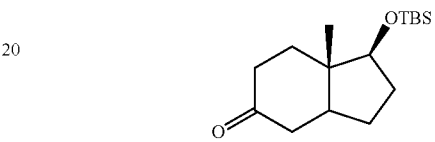

The appropriate 4-bromophenol (25 mmol) and imidazole (1.25 equiv.) were dissolved in a 1:1 DMF/THF solution (15 mL). TBDMSCl (1.25 equiv.) and DMAP (trace) were added and the reaction mixture was stirred overnight at room temperature. The mixture was diluted with distilled water (75 mL) and ether (75 mL) and then extracted with ethyl acetate (3×75 mL). The organic extracts were combined, dried over MgSO$_4$, filtered, and evaporated in vacuo. The crude product was purified on a flash column. Elution with hexane afforded of the desired product as a clear colorless oil in generally greater than 90% yield. All compounds produced by this route had $^1$H and $^{13}$C NMR spectra in agreement with the desired structures.

Protection of the Bromophenols as MOM Ethers:

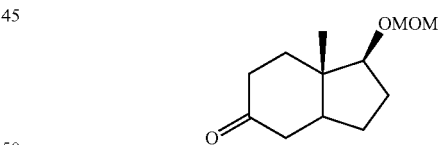

N,N-diisopropylethylamine (49.7 mmol) and chloromethyl methyl ether (49.7 mmol) were added to a solution of 4-bromophenol (24.9 mmol) in 30 ml of dry dichloromethane (DCM) under nitrogen atmosphere at 0° C. The resulting yellow mixture was stirred for 30 min. at 0° C. then left over night at room temperature. The organic mixture was diluted with aq. 10% NaOH (30 ml) and extracted with dichloromethane (3×30 mL). The organic layers were combined, dried over MgSO$_4$, filtered and concentrated in vacuo. The crude product was purified on a silica column. Elution with 15% ethylacetate in hexane afforded the desired product as yellowish oil with yields approaching 97%. All compounds produced by this route had $^1$H and $^{13}$C NMR spectra in agreement with the desired structures.

Protection of the 17-OH Group in the Hajos-Parrsish Ketone as its TBDMS Ether:

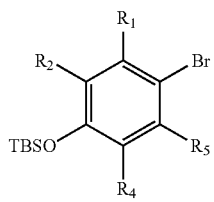

To a solution of the Hajos-Parrish ketone (17.85 mmol) in dimethylformamide (20 mL) was added imidazole (35.7 mmol) and TBDMSCl (19.23 mmol). The reaction mixture was stirred at room temperature for 1 h. The reaction mixture was diluted with EtOAc and washed with water and brine. The organic layers were combined, dried over MgSO$_4$, filtered and concentrated in vacuo. The crude yellow oil was purified on a silica column. Purification of crude product afforded the desired product as clear oil in 90% yield. $^1$H NMR (300 MHz, CDCl$_3$) δ 3.80 (t, J=4.8 Hz, 1H), 2.41 (m, 2H), 2.23 (m, 3H), 1.96 (m, 2H), 1.62 (m, 3H), 1.90 (m, 1H), 1.09 (s, 3H), 0.89 (s, 9H), 0.04 (s, 6H); ppm; $^{13}$C NMR (CDCl$_3$, 75 MHz) δ 213.4, 79.8, 43.5, 43.4, 42.3, 36.8, 32.3, 32.1, 28.3, 25.7, 20.3, 18.0, −4.5, −4.9 ppm; Mass (EI) m/z 282 (0.9%, M$^+$), 267 (3.8%), 225 (100%); HREIMS m/z. Found for C$_{16}$H$_{30}$O$_2$Si: 282.2053.

Protection of the 17-OH Group in the Hajos-Parrish Ketone as its MOM Ether:

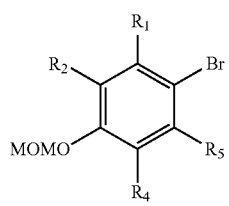

To a solution of Hajos-Parrish ketone (5.95 mmol) and chloromethyl methyl ether (7.73 mmol) dissolved in DCM (15 mL) under nitrogen atmosphere was added N,N-diisopropylethylamine (7.14 mmol) at 0° C. The resulting reaction mixture was stirred for 2 hrs at room temperature. The reaction mixture was diluted with brine (10 mL) and water (5 mL) and extracted with DCM (3×10 mL). The organic layers were combined, dried over MgSO$_4$, filtered and concentrated under vacuo. The crude yellow gummy product was purified on flash column, eluting with 30% ethylacetate in hexane afforded the desired product as colorless oil in 75% yield. $^1$H NMR (400 MHz, CDCl$_3$) δ 4.58 (m, 1H), 3.69 (t, J=5.7 Hz, 1H), 3.30 (s, 3H), 2.43-2.28 (m, 2H), 2.34-2.07 (m, 3H), 2.05-1.82 (m, 2H), 1.69-1.52 (m, 3H), 1.10 (s, 3H) ppm; $^{13}$C NMR (400 MHz, CDCl$_3$) δ 212.5, 95.4, 83.9, 77.3, 77.0, 76.7, 55.1, 43.8, 42.5, 42.2, 36.5, 32.3, 28.9, 28.1, 20.2 ppm.

Preparation of Enol Triflates of TBDMS Protected Hajos-Parrish Ketone:

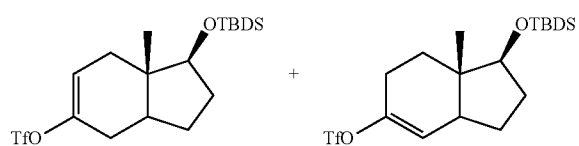

To a cold (−78° C.) solution of lithium diisopropylamide (2.65 mmol) in THF (10 mL) was added slowly TBDMS protected Hajos-Parrish ketone (1.77 mmol) in THF (5 mL). After one hour at this temperature, a solution of N-(phenyl) triflimide (2.12 mmol) in THF (5 mL) was introduced, and the reaction mixture was allowed to warm to room temperature for 2 h. The resulting mixture was quenched with NH$_4$Cl (15 mL) and extracted with ether (3×15 mL). The organic phase was dried over MgSO$_4$ and the solvents were evaporated under vacuo. The residue was purified by silica gel column chromatography eluting with hexane to afford colorless oil (70%). $^1$H NMR (400 MHz, CDCl$_3$) δ 5.62 (m, 1H), 3.71 (m, 1H), 1.9-2.4 (m, 7H), 1.2-1.6 (m, 4H), 0.92 (s, 3H), 0.86 (s, 9H), 0.01 (s, 6H); ppm; $^{13}$C NMR (CDCl$_3$, 100 MHz) δ 147.6, 122.0, 79.2, 43.2, 42.9, 39.8, 32.3, 31.1, 30.0, 28.1, 27.7, 25.8, 24.6, 20.0, 19.5, −4.5, −4.9 ppm; Mass (EI) m/z 414.15, (100%, M$^+$) HREIMS m/z. Found for C$_{17}$H$_{29}$F$_3$O$_4$SSi: 414.1508.

Coupling of a Protected A Ring Moiety with Unprotected Hajos-Parrish Ketone: General Procedure A.

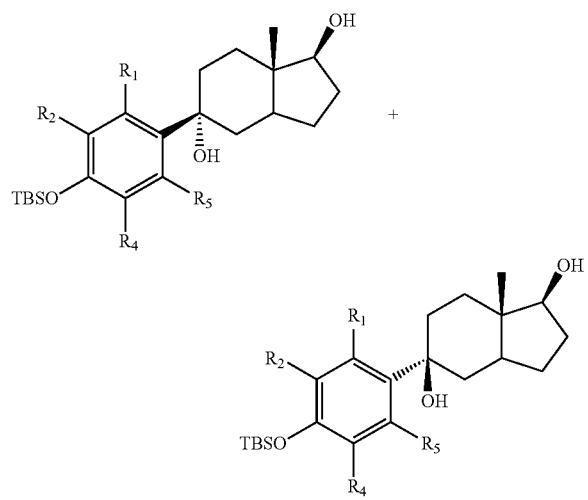

Protected bromophenol derivative (8.92 mmol) was dissolved in dry THF (20 mL) under nitrogen. The solution was placed in a Dry Ice/acetone bath (−78° C.) and n-butyllithium (8.92 mmoL) was added drop wise. The solution was stirred for 5 minutes and a solution of unprotected Hajos-Parrish ketone (2.97 mmol), dissolved in dry THF (2 mL), and added drop wise. The reaction mixture was quenched after 10 min with sat. NH$_4$Cl solution (10 mL) and of water (10 mL). The solution was extracted with EtOAc (3×30 mL), dried over MgSO$_4$, filtered and evaporated under vacuo. Flash chromatography of the crude product starting the elution with 30% EtOAc: hexane to 50% EtOAc: hexane generally allowed one to separated cleanly both steroisomers with overall yields approaching 80%. The isomer having the A ring in the equatorial position relative to the CD ring eluted first. All compounds produced by this route had $^1$H and $^{13}$C NMR spectra in agreement with the desired structures.

Coupling of a Protected A Ring Moiety with Either MOM or TBDMS Hajos-Parrish Ketone: General Procedure B.

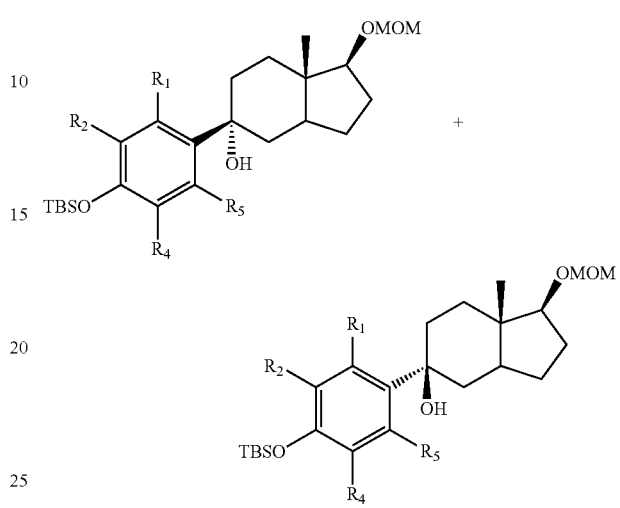

A suitably protected bromophenol (2.94 mmol) was dissolved in dry THF (20 mL) and placed in a Dry Ice/acetone bath (−78° C.). n-Butyllithium (2.94 mmol) was added drop wise and the solution was left to stir for 5 minutes. A protected CD ring (1.67 mmol) was dissolved in dry THF (2 mL) and added drop wise. After 10 min., the reaction mixture was quenched with sat NH$_4$Cl solution (10 mL) and water (10 mL). The solution was extracted with EtOAc (3×30 mL), dried over MgSO$_4$, filtered and evaporated under vacuo. The crude product was eluted with 5% EtOAc: hexane to 10% EtOAc: hexane on silica gel column afforded a mixture of both isomers, typically in 75% yield. All compounds produced by this route had $^1$H and $^{13}$C NMR spectra in agreement with the desired structures.

Dehydration and Deprotection of the A-CD Coupled Products. General Procedure C.

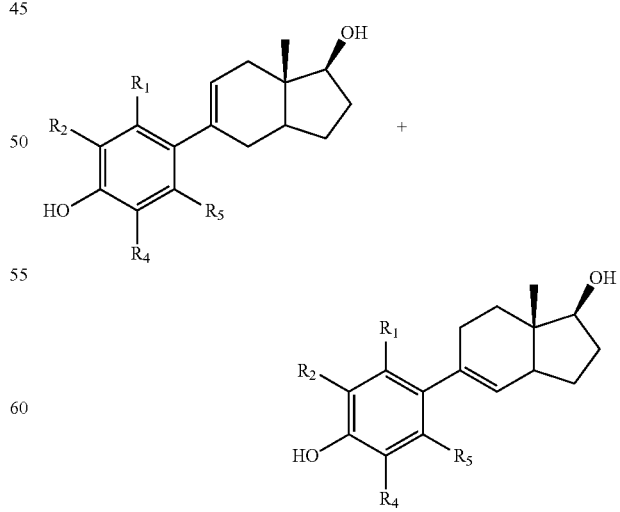

A mixture of both isomers (0.146 mmol) of the condensation products of A and CD rings obtained using one of the two general procedures A or B described above was dissolved in toluene (2 mL). A trace of para toluenesulfonic acid (PTSA) was added. The solution was kept at room temperature until TLC showed the disappearance of the starting material. The mixture was concentrated in vacuo and subjected to silica gel column chromatography. Elution with 20% ethyl acetate: 80% hexane afforded a mixture of both isomers usually in more than 85% yield.

The above dehydration mixture (0.130 mmol) was dissolved in THF (3 mL) and TBAF (0.130 mmol) was added to the solution drop wise. The resulting mixture was left for 10 min, diluted with brine (1 mL) and water (1 mL) and extracted with EtOAc (3×10 mL). The organic layers were combined, dried over MgSO$_4$, filtered, and concentrated in vacuo. The crude product was subjected to a silica gel column chromatography. Elution with 25% EtOAc: 75% hexane afforded the product mixture, generally in greater than 80% yield. All compounds produced by this route had $^1$H and $^{13}$C NMR spectra in agreement with the desired structures.
Deprotection of the Initial A-CD Ring Coupled Products. Retaining the 9-OH Group. General Procedure D.

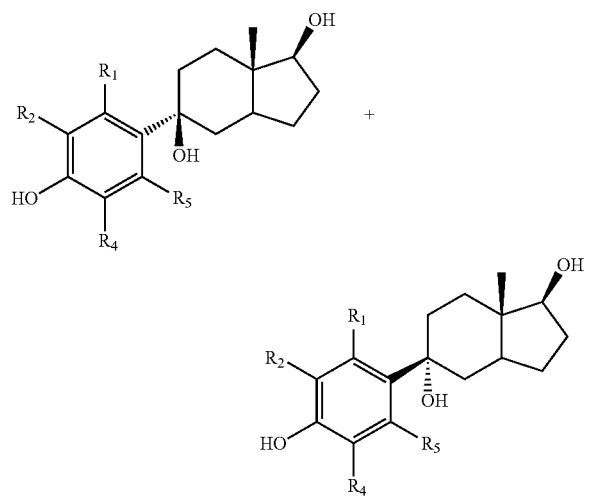

A mixture of both isomers from condensation product of A and CD ring (0.127 mmol) produced by the general procedure A, above, in which the bromophenol was protected as its TBDMS derivative was dissolved in THF (2 mL). A THF solution of TBAF (0.127 mmol) was added, the mixture was kept for 10 minutes then diluted with brine (1 mL) and water (1 mL) and extracted with EtOAc (3×5 mL). The organic layers were combined, dried over MgSO$_4$, filetered, and concentrated in vacuo. The crude product was subjected to a silica gel column eluting with 25% EtOAc: 75% hexane to afford the desired product mixture, generally in greater than 90% yield. All compounds produced by this route had $^1$H and $^{13}$C NMR spectra in agreement with the desired structures.
Hydrogenation of the C-Ring Alkenes: General Procedure E

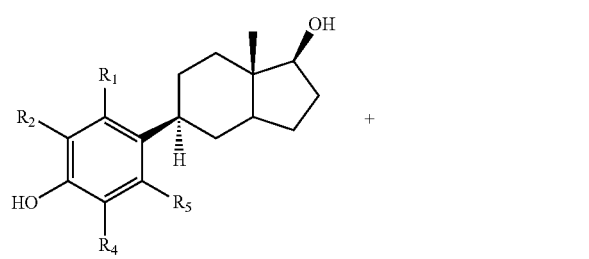

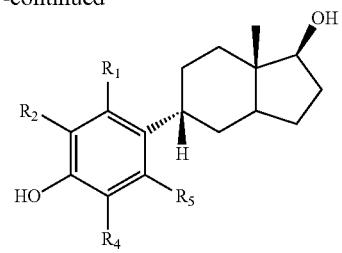

To a solution of unsaturated C-ring alkene ACD adduct (0.38 mmol) dissolved in methanol (5.0 mL) was added about 5-10% by weight of Pd (10% on carbon). The mixture was stirred under hydrogen atmosphere for 2 h, filtered through Celite pad and washed several times with EtOAc. The solvent was evaporated under vacuo to afford white solid. The crude was purified by column chromatography eluting with 45% EtOAc in hexanes afforded as a white solid with a generally more than 95% yield. In most instances the two isomers were separable by this procedure. In some cases the separation needed to be carried out using a preparative HPLC system. All compounds produced by this route had $^1$H and $^{13}$C NMR spectra in agreement with the desired structures. Those of the key ACD compounds having the desired natural stereochemistry at C9 are recorded below.

Example 5

Selected Estrogenic Compounds Synthesized by Sequence and Procedures Described in Example 4

The entry numbers are used to refer to the compounds recited in the tables in the following Examples.
NMR Data for Compound, Entry 1:

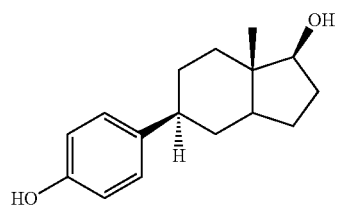

$^1$H NMR (400 MHz, Acetone-d$_6$) δ 8.17 (OH), 7.07 (d, J=8.5 Hz, 2H), 6.76 (d, J=8.5 Hz, 2H), 3.67 (brs, 1H), 2.65 (m, 1H), 2.21 (m, 1H), 2.09 (m, 1H), 1.80 (m, 2H), 1.65 (m, 5H), 1.30 (m, 1H), 1.24 (m, 1H), 1.35 (s, 3H); ppm; $^{13}$C NMR (Acetone-d$_6$, 100 MHz) δ 157.1, 140.0, 129.4, 116.7, 83.2, 45.6, 43.3, 39.0, 34.2, 34.0, 33.7, 31.4, 28.2, 19.9 ppm; Mass (EI) m/z 246 (48.3%, M$^+$), 228 (2.5%), 202 (4.2%), 146 (10.9%), 120 (100%); HREIMS m/z calculated for C$_{16}$H$_{22}$O$_2$ 246.1779.
NMR Data for Compound, Entry 2:

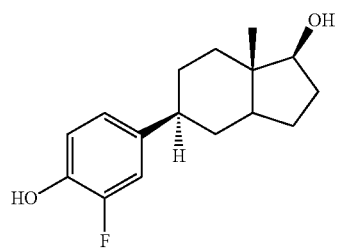

¹H NMR (400 MHz, Acetone-d₆): 0.90 (3H, s), 1.12-1.39 (4H, m), 1.56-1.62 (4H, m), 1.72 (1H, quintet, J=6.24 Hz), 1.92 (1H, dt, J=13.73 and 3.09 Hz), 2.37-2.45 (1H, m), 3.44 (1H, d, J=5.60 Hz), 4.36-4.41 (1H, m), 6.84-6.91 (2H, m), 6.94-6.97 (1H, m), 8.33 (1H, s); ¹³C NMR (100 MHz, Acetone-d₆): 24.0, 28.6, 34.9, 40.9, 44.4, 44.7, 46.9, 73.9, 115.7, 115.9, 119.3, 119.4, 124.4, 124.4, 141.8, 141.9, 152.0 ppm.
NMR Data for Compound, Entry 3:

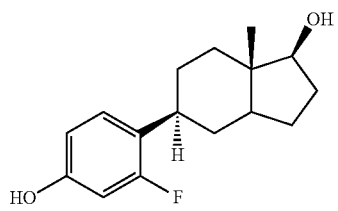

¹H NMR (400 MHz, Acetone-d₆): 0.91 (3H, s), 1.13-1.20 (1H, m), 1.25-1.32 (1H, m), 1.37 (1H, dd, J=13.10 and 4.62 Hz), 1.53-1.68 (4H, m), 1.74 (1H, quintet, J=6.20 Hz), 1.93 (1H, dt, J=13.78 and 3.21 Hz), 2.09-2.15 (1H, m), 2.69 (1H, tt, J=12.23 and 3.21 Hz), 2.89 (1H, s), 3.45 (1H, d, J=5.04 Hz), 4.36-4.40 (1H, m), 6.52 (1H, dd, J=12.26 and 2.46 Hz), 6.60 (1H, dd, J=8.40 and 2.43 Hz), 7.10 (1H, t, J=8.63 Hz), 8.49 (1H, s); ¹³C NMR (100 MHz, Acetone-d₆,): 24.0, 28.6, 30.1, 34.9, 37.8, 37.9, 39.5, 44.4, 46.9, 73.9, 104.2, 104.5, 113.0, 113.1, 126.3, 126.5, 129.8, 129.9, 158.5, 158.6, 161.6, 164.0 ppm.
NMR Data for Compound, Entry 4:

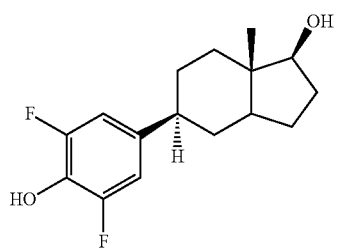 [SMILES: C[C@]12CC[C@H](c3cc(F)c(O)c(F)c3)CC1CC[C@@H]2O]

¹H NMR (400 MHz, CDCl₃): 1.10 (3H, s), 1.24-1.28 (3H, m), 1.46-1.57 (2H, m), 1.69-1.77 (2H, m), 1.82-1.91 (1H, m), 2.06-2.13 (1H, m), 2.18-2.27 (1H, m), 2.61 (1H, tt, J=12.38 and 3.69 Hz), 3.73 (1H, d, J=5.84 Hz), 5.22 (1H, s), 6.76 (2H, d, J=9.00 Hz); ¹³C NMR (100 MHz, CDCl₃): 18.3, 26.5, 29.2, 31.7, 32.0, 31.2, 37.4, 41.3, 44.0, 82.4, 109.7, 109.8, 109.8, 109.9, 110.0, 130.6, 139.5, 150.4, 150.4, 152.8, 152.8 ppm.
NMR Data for Compound, Entry 5:

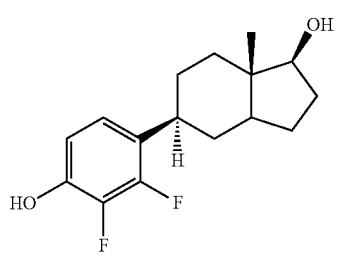 [SMILES: C[C@]12CC[C@H](c3ccc(O)c(F)c3F)CC1CC[C@@H]2O]

¹H NMR (400 MHz, Acetone-d₆): 1.12 (3H, s), 1.22-1.28 (1H, m), 1.35 (1H, td, J=13.24 and 3.90 Hz), 1.54-1.62 (2H, m), 1.64-1.74 (3H, m), 1.76-1.84 (2H, m), 2.08-2.13 (1H, m), 2.18-2.27 (1H, m), 3.01 (2H, tt, J=12.35 and 3.84 Hz), 3.65 (1H, d, J=5.66 Hz), 6.76 (1H, td, J=8.42 and 1.96 Hz), 6.95 (1H, td, J=8.19 and 2.26 Hz); ¹³C NMR (100 MHz, Acetone-d₆): 20.0, 28.2, 29.9, 32.7, 32.8, 33.9, 34.0, 43.3, 45.8, 83.2, 114.4, 114.4, 123.2, 123.2, 123.2, 123.3, 128.1, 128.1, 128.2, 128.3, 140.8, 143.2, 143.4, 146.0, 146.1, 146.1, 146.2, 150.0, 152.4 ppm.
NMR Data for Compound, Entry 7:

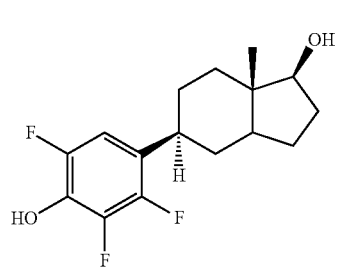

¹H NMR (400 MHz, Acetone-d₆): 1.14 (3H, s), 1.33 (2H, m), 1.69 (4H, m), 1.85 (2H, m), 2.10 (1H, m), 2.26 (1H, m), 3.03 (1H, m), 3.66 (1H, d, J=5.66 Hz), 6.85 (1H, m) ppm.
NMR Data for Compound, Entry 8:

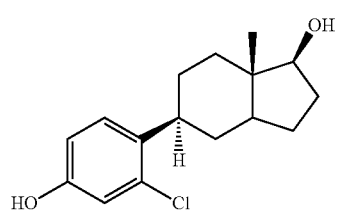

¹H NMR (400 MHz, Acetone-d6) δ 7.15 (d, J=8.8 Hz, 1H), 6.84 (d, J=2.4 Hz, 1H), 6.75 (dd, J=8.4, 2.4 Hz, 1H), 4.38 (t, J=8.0 Hz, 1H), 3.48(m, 1H), 1.96-1.12 (m, 18H), 0.91 (s, 3H) ppm.
NMR Data for Compound, Entry 9:

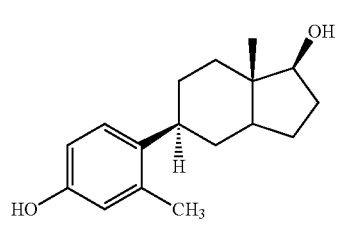 [SMILES: Cc1cc(O)ccc1[C@H]1CC[C@@]2(C)C(CC[C@@H]2O)C1]

¹H NMR (400 MHz, Acetone-d₆): 1.14 (3H, s), 1.23-1.29 (1H, m), 1.36 (1H, td, J=13.24 and 3.78 Hz), 1.48-1.54 (1H, m), 1.58-1.62 (3H, m), 1.64-1.71 (1H, m) 1.80-1.87 (2H, m), 2.23 (3H, s), 2.90 (3H, s), 3.42 (1H, d, J=4.25 Hz), 3.65 (1H, t, J=4.74 Hz), 6.61-6.64 (2H, m), 7.08 (1H, d, J=8.34 Hz), 7.93 (1H, s); ¹³C NMR (100 MHz, Acetone-d₆): 20.2, 20.4, 28.4, 33.9, 34.0, 34.6, 34.8, 43.7, 45.9, 83.3, 114.7, 118.8, 128.1, 138.0, 138.0, 156.8 ppm.

NMR Data for Compounds, Entry 11:

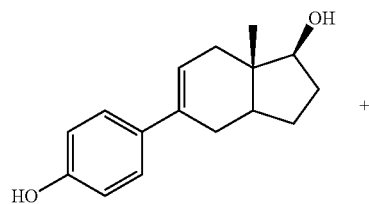

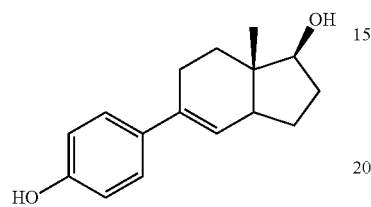

¹H NMR (400 MHz, Acetone-d₆) δ 8.34 (OH), 7.36 (d, J=8.8 Hz, 2H), 6.88 (d, J=8.8 Hz, 2H), 6.06 (m, 1H), 3.88 (m, 1H), 2.47 (m, 2H), 2.19 (m, 2H), 1.89 (m, 1H), 1.71 (m, 2H), 1.45 (m, 2H), 1.09 (s, 3H); ppm; ¹³C NMR (Acetone-d₆, 100 MHz) δ 158.3, 135.6, 128.0, 121.7, 116.9, 79.6, 46.4, 44.3, 34.7, 32.4, 30.3, 29.5, 26.0, 21.3 ppm; Mass (EI) m/z 244 (100%, M⁺), 211 (9.1%), 185 (35.5%), 146 (33.0%), 120 (44.6%); HREIMS m/z calculated for C₁₆H₂₀O₂ 244.1445.

NMR Data for Compounds, Entry 12:

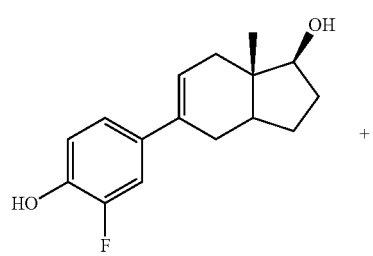

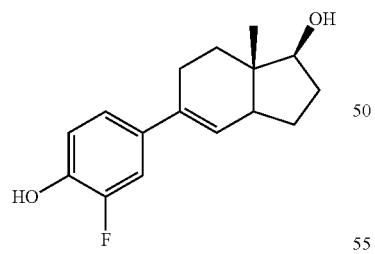

¹H NMR (400 MHz, Acetone-d₆): 0.98 (3H, s), 1.29-1.37 (1H, m), 1.41-1.48 (1H, m), 1.57-1.64 (1H, m), 2.10-2.18 (1H, m), 2.30-2.38 (2H, m), 2.90 (2H, s), 3.52-3.59 (1H, m), 3.73-3.85 (1H, m), 5.98-6.04 (1H, m), 6.92 (1H, dd, J=9.21 and 8.52 Hz), 7.07-7.10 (1H, m), 7.15 (1H, dd, J=13.09 and 2.12 Hz), 8.53 (1H, s); ¹³C NMR (100 MHz, Acetone-d₆): 19.2, 19.8, 23.8, 27.3, 30.2, 31.7, 32.0, 32.7, 39.8, 42.2, 42.3, 44.4, 77.6, 79.3, 112.3, 112.3, 112.4, 112.5, 117.4, 117.4, 120.9, 120.9, 121.0, 121.2, 127.4, 132.7, 132.7, 134.7, 134.7, 143.4, 143.6, 150.1, 152.5 ppm.

NMR Data for Compounds, Entry 13:

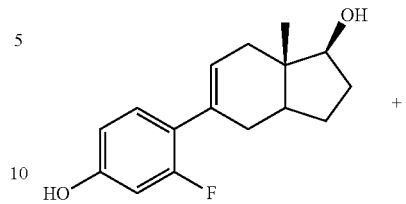

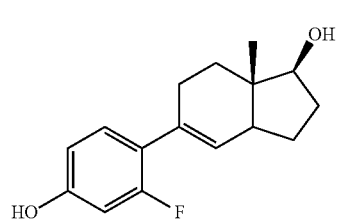

¹H NMR (400 MHz, Acetone-d₆): 1.00 (3H, s), 1.29-1.45 (2H, m), 1.55-1.63 (2H, m), 2.30-2.35 (2H, m), 2.90 (2H, s), 3.52-3.59 (1H, m), 3.73-3.88 (1H, m), 5.74-5.80 (1H, m), 6.54 (1H, dd, J=12.80 and 2.40 Hz), 6.62 (1H, dd, J=8.42 and 2.45 Hz), 7.10 (1H, t, J=8.59 Hz), 8.66 (1H, s); ¹³C NMR (100 MHz, Acetone-d₆): 19.3, 20.0, 25.5, 25.5, 28.1, 31.7, 31.9, 32.7, 40.0, 42.1, 44.3, 77.6, 79.3, 102.7, 102.9, 111.2, 111.2, 124.5, 129.8, 129.8, 129.9, 130.6, 130.6, 131.0, 131.0, 157.5, 157.6.

NMR Data for Compounds, Entry 14:

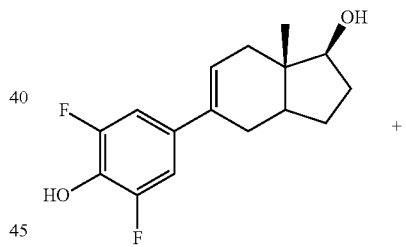

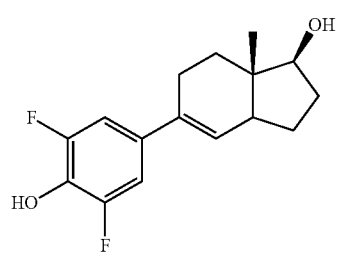

¹H NMR (400 MHz, CDCl₃,): 1.00 (3H, s), 1.30-1.42 (1 H, m), 1.45-1.67 (3H, m), 2.11-2.23 (2H, m), 2.30-2.41 (2H, m), 3.81-3.90 (1H, m), 5.95-6.02 (1H, m), 6.93 (2H, dd, J=1.82 and 9.92 Hz); ¹³C NMR (100 MHz, CDCl₃): 19.1, 19.8, 23.8, 27.0, 28.2, 28.9, 29.9, 31.7, 32.0, 32.5, 39.5, 42.5, 44.1, 79.2, 80.5, 108.0, 108.1, 108.2, 122.4, 128.6, 131.4, 131.9, 131.9, 134.1, 150.4, 150.5, 152.8, 152.9 ppm.

NMR Data for Compounds, Entry 15:

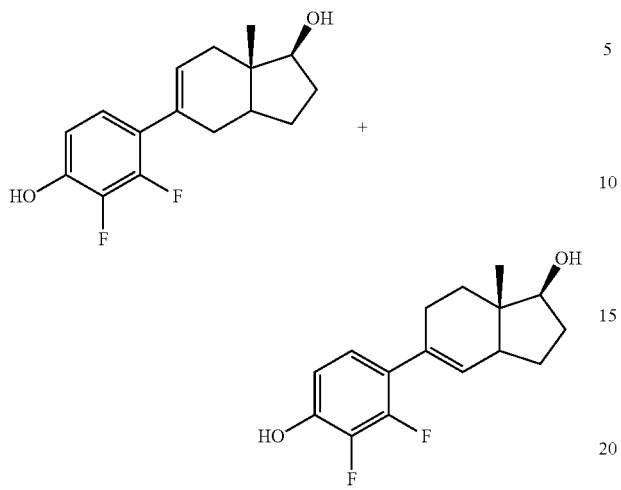

$^1$H NMR (400 MHz, Acetone-d$_6$): 1.01-1.04 (3H, m), 1.29-1.36 (1H, m), 1.38-1.46 (1H, m), 1.51-1.66 (2H, m), 2.10-2.19 (1H, m), 2.31-2.38 (2H, m), 2.92 (1H, s), 3.54-3.61 (1H, m), 3.74-3.87 (1H, m), 5.81-5.87 (1H, m), 6.73-6.78 (1H, m), 6.91 (1H, td, J=8.19 and 2.30 Hz), 9.00 (1H, s);
$^{13}$C NMR (100 MHz, Acetone-d$_6$): 21.2, 21.8, 27.2, 27.2, 32.1, 33.6, 33.7, 34.5, 41.8, 43.9, 44.0, 46.1, 79.5, 81.1, 114.2, 114.2, 114.3, 124.6, 124.6, 124.7, 127.6, 127.6, 131.9, 133.6, 133.6, 141.0, 141.2, 143.4, 146.8, 146.8, 146.9, 146.9, 149.5, 151.8 ppm.

NMR Data for Compound, Entry 16:

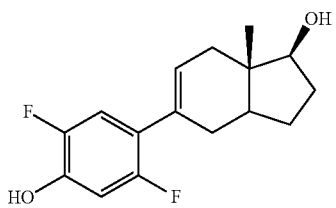 [SMILES: C[C@]12CC=C(c3cc(F)c(O)cc3F)CC1CC[C@@H]2O]

$^1$H NMR (400 MHz, Acetone-d$_6$) δ 7.01 (dd, J=11.6; 7.2 Hz, 1H), 6.72 (dd, J=11.6, 7.2 Hz, 1H), 5.82 (m, 1H), 3.73 (dd, J=6.4, 2.4 Hz, 1H), 2.22-2.07 (m, 6H), 1.93 (dq, 1H), 1.84-1.74 (m, 2H), 1.56-1.48 (m, 1H), 1.43-1.29 (m, 2H), 1.03 (s, 3H); $^{13}$C NMR (400 MHz, Acetone-d$_6$) δ 212.5, 95.4, 83.9, 77.3, 77.0, 76.7, 55.1, 43.8, 42.5, 42.2, 36.5, 32.3, 28.9, 28.1, 20.2 ppm.

NMR Data for Compound Entry 17:

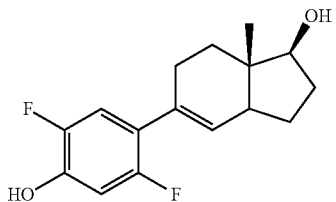 [SMILES: C[C@]12CCC(c3cc(F)c(O)cc3F)=CC1CC[C@@H]2O]

$^1$H NMR (400 MHz, Acetone-d$_6$) δ 6.98 (dd, J=11.6; 7.2 Hz, 1H), 6.63 (dd, J=11.6, 7.6 Hz, 1H), 5.83 (dd, J=2.0, 2.0 Hz, 1H), 3.81 (t, J=6.0 Hz, 1H), 2.37-2.22 (m, 3H), 2.13-1.97 (m, 7H), 1.59-1.51 (m, 2H), 1.41-1.27 (m, 2H), 0.96 (s, 3H); $^{13}$C NMR (400 MHz, Acetone-d$_6$) δ 131.7, 115.6, 115.5, 115.4, 115.3, 115.2, 105.2, 104.9, 77.5, 44.3, 25.3, 25.2, 19.3 ppm.

NMR Data for Compounds, Entry 18:

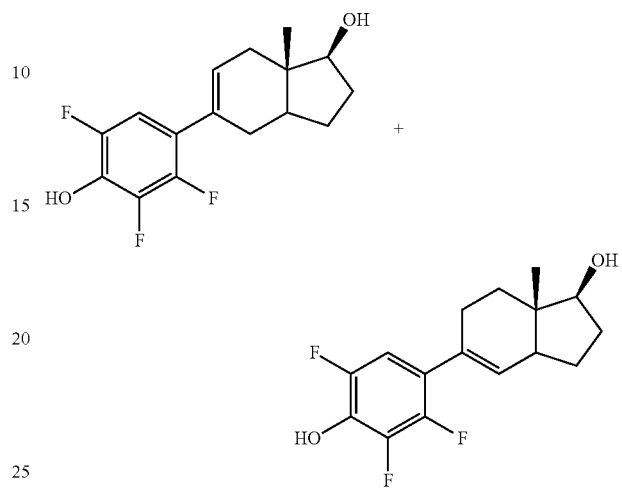

$^1$H NMR (400 MHz, Acetone-d$_6$): 0.99 (3H, s), 1.28-1.89 (6H, m), 2.10-2.34 (6H, m), 3.83 (1H, m), 5.86 (1H, m), 6.78 (1H, m) ppm.

NMR Data for Compound Entry 19:

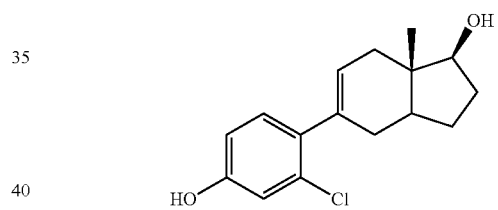

$^1$H NMR (400 MHz, Acetone-d6) δ 7.01 (d, J=8.4 Hz, 1H), 6.84 (d, J=2.4 Hz, 1H), 6.74 (dd, J=8.4, 2.4 Hz, 1H), 5.50 (m, 1H), 3.75 (dd, J=6.0, 1.6 Hz, 1H), 2.39 (m, 1H), 2.23-2.03 (m, 5H), 1.88 (dq, 1H), 1.84-1.77 (m, 1H), 1.75-1.69 (m, 1H), 1.56-1.44 (m, 2H), 1.07 (s, 3H) ppm;
$^{13}$C NMR (Acetone-d6, 100 MHz) δ 157.0, 135.0, 134.0, 132.3, 130.8, 124.7, 116.0, 114.1, 79.3, 42.1, 39.8, 32.2, 31.8, 29.7, 29.6, 29.4, 29.3, 29.2, 29.0, 28.8, 28.6, 28.4, 28.0, 19.8 ppm.

NMR Data for Compound Entry 20:

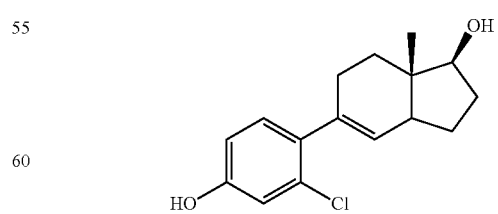

$^1$H NMR (400 MHz, Acetone-d6) δ 7.02 (d, J=8.4 Hz, 1H), 6.85 (d, J=2.4 Hz, 1H), 6.74 (dd, J=8.4, 2.4 Hz, 1H), 5.55 (m, 1H), 3.88 (t, J=6.0 Hz, 1H), 2.33-2.02 (m, 7H), 1.65-1.57 (m, 2H), 1.44-1.29 (m, 2H), 1.02 (s, 3H) ppm; $^{13}$C NMR (400

MHz, Acetone-d6) δ 156.8, 134.8, 134.3, 132.3, 131.0, 130.8, 115.9, 114.1, 77.5, 44.1, 42.2, 31.9, 30.2, 29.7, 29.5, 29.4, 29.2, 29.0, 28.8, 28.7, 28.6, 28.4, 26.3, 19.4 ppm.

NMR Data for Compound, Entry 21:

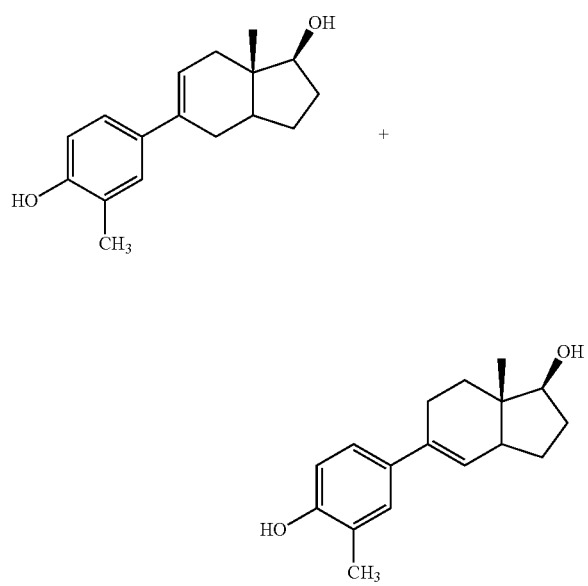

$^1$H NMR (400 MHz, CDCl$_3$): 1.00 (3H, s), 1.17-1.25 (1H, m), 1.34-1.42 (2H, m), 2.11-2.17 (2H, m), 2.25 (4H, m), 2.37-2.40 (2H, m), 3.79-3.90 (1H, m), 4.65 (1H, s), 5.89-5.97 (1H, m), 6.72 (1H, d, J=8.19 Hz), 7.11 (1H, dt, J=8.10 and 2.26 Hz), 7.17 (1H, m) ppm.

NMR Data for Compounds Entry 22:

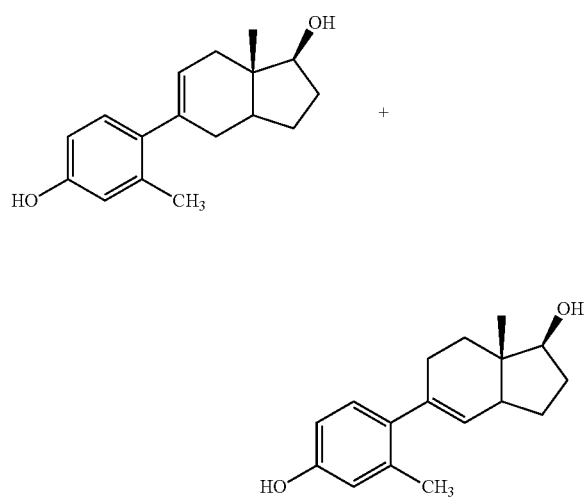

$^1$H NMR (400 MHz, CDCl$_3$): 1.04-1.09 (3H, m), 1.33-1.47 (2H, m), 1.49-1.73 (4H, m), 1.77-1.90 (1H, m), 2.05-2.17 (3H, m), 2.30-2.37 (1H, m), 3.82-3.95 (1H, m), 5.41-5.50 (1H, m), 6.60 (1H, dd, J=8.15 and 2.60 Hz), 6.64 (1H, d, J=2.55 Hz), 6.91 (1H, dd, J=8.14 and 3.22 Hz); $^{13}$C NMR (100 MHz, CDCl$_3$): 19.4, 19.8, 19.9, 27.1, 28.3, 29.1, 30.2, 30.3, 31.9, 32.2, 39.7, 42.2, 42.4, 43.9, 79.3, 80.7, 112.3, 116.7, 123.1, 129.4, 129.5, 129.6, 135.8, 135.9, 136.7, 136.7, 136.8, 154.1 ppm.

NMR Data for Compound, Entry 24:

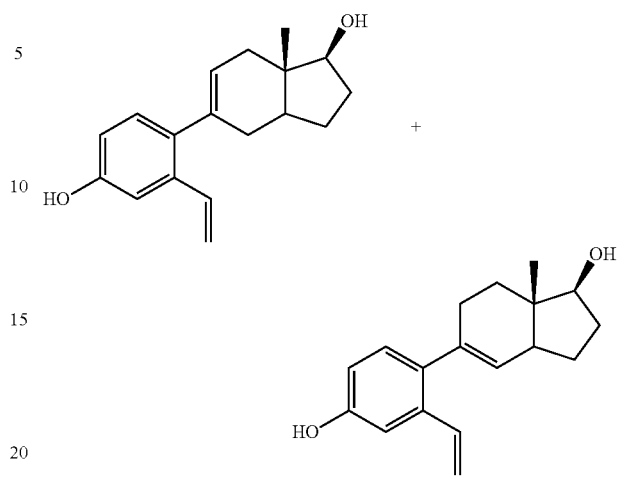

$^1$H NMR (CDCl$_3$, 400 MHz): δ 7.00 (dd, apparent t, J=2.8, 2.8 Hz, 1H), 6.96 (dd, J=8.0, 1.2, 1H), 6.83-6.75 (m, 1H), 6.72-6.69 (m, 1H), 5.61 (dd, J=17.6, 1.2 Hz, 1H), 5.46-5.44 (m, 1H), 5.20 (dd, J=10.8, 1.2 Hz, 1H), 3.94 (dd, apparent t, J=5.6, 5.6, 0.4 H), 3.85 (dd, J=6.4, 1.6 Hz, 0.6 H), 2.39-2.08 (m, 4H), 1.91-1.83 (m, 1H), 1.81-1.19 (m, 7H), 1.09 (s, 1.8H), 1.05 (s, 1.2H); $^{13}$C NMR (CDCl$_3$, 100 MHz): δ 154.42, 136.60, 136.57, 136.12, 135.97, 135.40, 135.32, 134.85, 134.78, 130.88, 129.80, 129.73, 124.50, 114.72, 114.68, 114.20, 114.15, 111.68, 111.54, 80.68, 79.29, 43.96, 42.36, 42.18, 39.76, 32.21, 32.10, 31.84, 30.77, 29.02, 28.23, 27.47, 19.94, 19.38 ppm.

NMR Data for Compound, Entry 27:

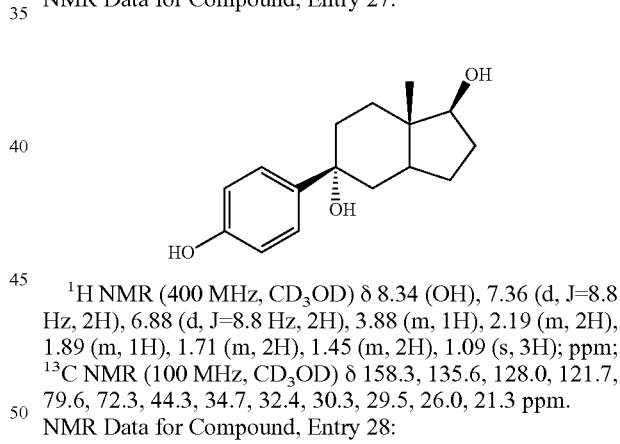

$^1$H NMR (400 MHz, CD$_3$OD) δ 8.34 (OH), 7.36 (d, J=8.8 Hz, 2H), 6.88 (d, J=8.8 Hz, 2H), 3.88 (m, 1H), 2.19 (m, 2H), 1.89 (m, 1H), 1.71 (m, 2H), 1.45 (m, 2H), 1.09 (s, 3H); ppm; $^{13}$C NMR (100 MHz, CD$_3$OD) δ 158.3, 135.6, 128.0, 121.7, 79.6, 72.3, 44.3, 34.7, 32.4, 30.3, 29.5, 26.0, 21.3 ppm.

NMR Data for Compound, Entry 28:

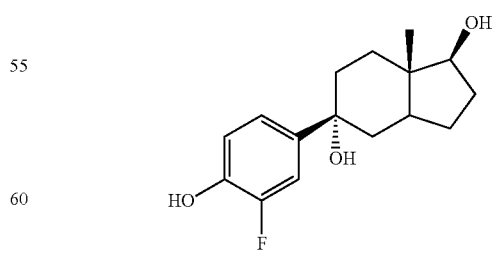

$^1$H NMR (400 MHz, Acetone-d$_6$): 1.02 (3H, s), 1.06-1.12 (1H, m), 1.48-1.54 (1H, m), 1.63-1.72 (2H, m), 1.75-1.85 (2H, m), 1.87-1.97 (2H, m), 2.09-2.21 (2H, m), 3.43 (1H, d, J=4.72 Hz), 3.64 (1H, s), 3.85-3.88 (1H, m), 6.92 (1H, t, J=8.55 Hz), 7.15 (1H, ddd, J=8.45, 2.24, and 0.92 Hz), 7.26 (1H, dd, J=13.22 and 2.23 Hz), 8.46 (1H, s); $^{13}$C NMR (100 MHz, Acetone-d$_6$): 20.9, 29.5, 33.5, 36.1, 40.2, 43.6, 45.1, 74.4, 80.9, 114.8, 115.0, 118.9, 118.9, 123.0, 123.0, 144.3, 144.3, 144.7, 144.9, 151.7, 154.1 ppm.

NMR Data for Compound, Entry 29:

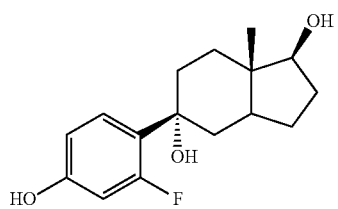 [SMILES: C[C@]12CC[C@](O)(c3ccc(O)cc3F)CC1CC[C@@H]2O]

$^1$H NMR (400 MHz, CD$_3$OD): 1.00 (3H, s), 1.06 (1H, dt, J=13.85 and 4.66 Hz), 1.45-1.61 (3H, m), 1.68-1.75 (1H, m), 1.79-1.85 (2H, m), 2.01-2.07 (1H, m), 2.14-2.25 (2H, m), 2.29-2.36 (1H, m), 3.27-3.28 (2H, m), 3.32 (1H, s), 3.81 (1H, dd, J=6.64 and 3.72 Hz), 6.42 (1H, dd, J=14.15 and 2.41 Hz), 6.52 (1H, dd, J=8.60 and 2.40 Hz), 7.32 (1H, t, J=9.63 Hz); $^{13}$C NMR (100 MHz, CD$_3$OD): 19.7, 29.1, 29.9, 32.5, 33.7, 33.8, 37.4, 37.5, 43.0, 44.5, 74.0, 74.1, 81.0, 104.3, 104.6, 111.7, 111.7, 127.3, 127.4, 129.2, 129.3, 159.0, 159.2, 160.9, 163.3 ppm.

NMR Data for Compound, Entry 30:

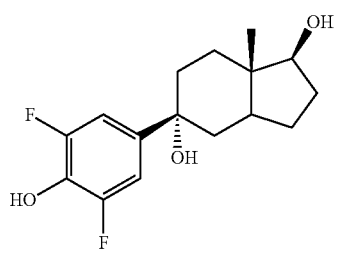 [SMILES: C[C@]12CC[C@](O)(c3cc(F)c(O)c(F)c3)CC1CC[C@@H]2O]

$^1$H NMR (400 MHz, CD$_3$OD): 0.95 (3H, s), 1.06-1.13 (1H, m), 1.21 (1H, t, J=7.14 Hz), 1.46-1.55 (1H, m), 1.60-1.76 (3H, m), 1.81-2.04 (5H, m), 2.13-2.22 (1H, m), 3.29 (2H, quintet, J=1.61 Hz), 3.90 (1H, dd, J=7.04 and 4.54 Hz), 6.99 (2H, d, J=10.21 Hz); $^{13}$C NMR (100 MHz, CD$_3$OD): 18.8, 27.2, 28.8, 30.6, 33.5, 37.8, 41.7, 42.9, 72.5, 78.5, 108.1, 108.1, 108.2, 108.3, 104.4, 139.4, 151.1, 151.1, 153.4, 153.5 ppm.

Example 6

Oxidation of 17-OH to Ketone and its Ethynyl Derivative (Entry 10)

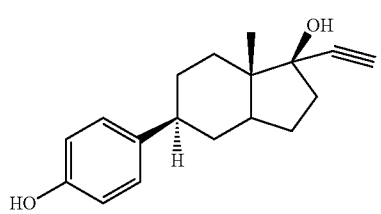 [SMILES: C#C[C@]1(O)CCC2C[C@@H](c3ccc(O)cc3)CC[C@@]21C]

To a solution of saturated final compound (0.2 mmol) in acetone (5 mL) was added Jones' reagent (0.22 mmol). The reaction was stirred at room temperature for 5 minutes. Iso- propanol (0.5 mL) was added, solvent was evaporated under vacuo and extracted with EtOAc (3×5 mL). The organic layers were combined, dried over MgSO$_4$ and evaporated under vacuo to give white gummy oil. Purification of crude product by flash chromatography afforded white solid with 90% yield. $^1$H NMR (400 MHz, Acetone-d$_6$) δ 8.08 (OH), 7.10 (d, J=8.5 Hz, 2H), 6.76 (d, J=8.5 Hz, 2H), 2.74 (m, 1H), 2.43 (m, 1H), 2.12 (m, 3H), 1.82 (m, 3H), 1.59 (m, 3H), 1.17 (m, 1H), 1.11 (s, 3H); ppm; $^{13}$C NMR (Acetone-d$_6$, 100 MHz) δ 207.1, 157.4, 139.6, 129.5, 116.9, 47.9, 45.0, 39.0, 37.5, 34.5, 30.4, 24.6, 20.2 ppm.

A solution of the above oxidized product (1.0 mmol) in dry dimethyl sulfoxide (10 mL) under nitrogen was treated with lithium acetylide-ethylenediamine complex (300 mg), and the mixture was stirred at room temperature for 16-20 h. The mixture was poured into cold water, acidified with dilute acetic acid, extracted with ethyl acetate, washed with water and brine, and dried over MgSO$_4$. After evaporation of the solvent under reduced pressure, the residue was chromatographed on silica gel with 10-20% ethyl acetate in hexane to yield the desired compound. $^1$H NMR (400 MHz, Acetone-d$_6$) δ 7.08 (d, J=8.4 Hz, 2H), 6.74 (d, J=8.4 Hz, 2H), 2.64 (m, 1H), 2.04 (m, 1H), 1.40-1.80 (m, 10H), 1.21 (s, 3H); ppm; $^{13}$C NMR (Acetone-d$_6$, 100 MHz) δ 155.4, 138.2, 127.7, 115.0, 88.3, 80.4, 73.0, 44.8, 42.1, 37.6, 37.3, 33.2, 29.8, 28.3, 23.1, 18.8 ppm.

Example 7

Synthesis of Unsaturated Compounds

Coupling of A Ring with Hajos-Parrish Derived Enol Triflate:

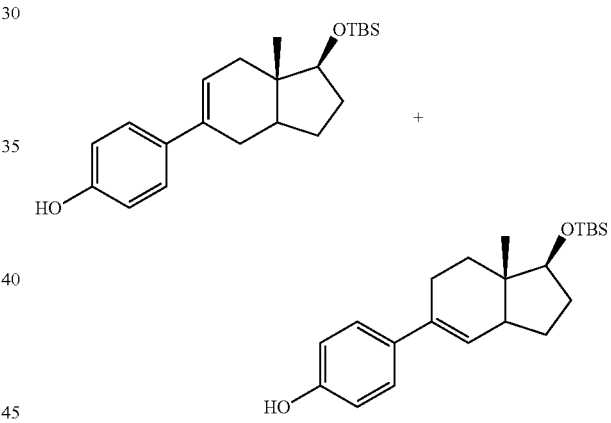

To a solution of enol triflate (3.38 mmol) and (dba)$_3$Pd$_2$.CHCl$_3$ (0.1 mmol) in DCM (18 mL) at −78° C. was added a solution of 4-hydroxyphenylboronic acid (3.37 mmol) in THF (30 mL) followed by addition of triethylamine (10 mmol). The reaction mixture was brought to room temperature and refluxed for 1 h at 80° C., concentrated and purified by flash chromatography on silica gel (10% EtOAc in hexanes) to give the compounds 11 as a colorless oil with 74% yield. $^1$H NMR (400 MHz, CDCl$_3$) δ 7.31 (d, J=9.0 Hz, 2H), 6.83 (d, J=9.0 Hz, 2H), 5.63 (m, 1H), 3.71 (m, 1H), 1.74-2.48 (m, 6H), 1.28-1.34 (m, 3H), 0.94 (s, 3H), 0.87 (s, 9H), 0.01 (s, 6H); ppm; $^{13}$C NMR (CDCl$_3$, 100 MHz) δ 158.4, 147.6, 127.4, 116.0, 79.2, 42.9, 39.8, 32.1, 31.1, 27.9, 25.8, 19.9, −4.5, −4.9 ppm.

Preparation of 5-vinyl-4-bromo-phenol

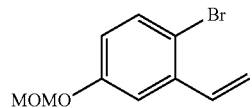

PPh₃MeBr (41.1 mmol) was dissolved in dry THF (120 ml) under nitrogen atmosphere for 15 min. at 0° C. A 1.0 M solution of NaHMDS (31.5 mmol) was added dropwise and the reaction mixture was stirred for 30 min at 0° C. The 4-bromo-5-benzaldehyde (24.2 mmol) in dry THF (10 ml) was added drop wise to the reaction mixture. The reaction mixture was stirred for 2 hours at room temperature and diluted with NH₄Cl (30 ml) and extracted with ether (3×30 mL). The organic layers were combined, dried over MgSO₄, filtered, and evaporated under vacuo. The crude product was purified by using silica gel to afford a pure compound as yellow oil with 91% yield. ¹H NMR (CDCl₃, 400 MHz): δ 7.44 (d, J=8.8 Hz, 1H), 7.24 (d, J=3.2, 1H), 7.02 (dd, J=17.6, 11.2, 1H), 6.85 (dd, J=8.8, 3.2 Hz, 1H), 5.71 (dd, J=17.6, 1.2, 1H), 5.37 (dd, J=10.8, 0.8 Hz, 1H), 5.17 (s, 2H), 3.48 (s, 3H) ppm; ¹³C NMR (CDCl₃, 100 MHz): δ 156.63, 138.24, 135.61, 133.41, 117.31, 116.83, 115.54, 114.37, 94.47, 55.98 ppm.

Reaction of Compound Entry 24 with Benzylmercaptan:

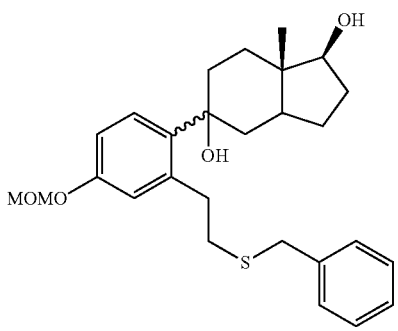

The benzylmercaptan (0.45 mmol) was added to compound entry 24 (0.301 mmol) in CDCl₃ (2.0 mL). The reaction mixture was exposed to the light for two weeks. The reaction mixture was evaporated under vacuo and subjected to flash chromatography to give the desired product in 69% yield. ¹H NMR (CDCl₃, 400 MHz): δ 7.34-7.19 (m, 6H), 6.81-6.78 (m, 2H), 5.11 (s, 2H), 4.25 (dd, J=8.0, 8.0 Hz, 1H), 3.68 (s, 2H), 3.44 (s, 3H), 3.31-3.23 (m, 1H), 3.20-3.13 (m, 1H), 2.69 (dd, J=8.0 Hz, 2H), 2.20-1.04 (m, 19H), 0.95 (s, 3H), 0.91-0.82 (m, 1H) ppm; ¹³C NMR (CDCl₃, 100 MHz): δ 155.93, 141.43, 139.57, 138.46, 128.87, 128.39, 126.86, 126.35, 119.54, 113.21, 94.26, 73.99, 73.64, 55.93, 42.56, 41.86, 40.67, 36.45, 34.20, 33.72, 33.60, 30.12, 28.17, 26.46, 21.54 ppm.

Preparation of Compounds Entry 25 and 26:

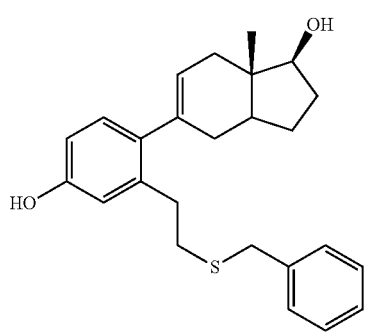

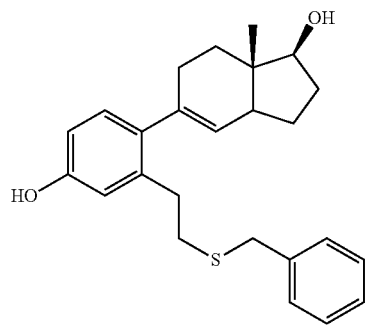

The adduct described above (0.206 mmol) was dissolved in THF (1.8 mL) and water (0.2 mL). A few crystals of para-toluene sulfonic acid were added and the reaction mixture was refluxed for 24 hours. The reaction mixture was diluted with sat. NaHCO₃ (10 mL) and extracted with dichloromethane (2×10 mL). The organic extracts were combined, dried over MgSO₄, filtered and concentrated under vacuo. The crude product was purified using column chromatography afforded the de-protected mixture of isomers as yellow solid with 79% yield. These two stereoisomers were separated by using preparative recycling HPLC equipped with reverse phase column (250×21.2 mm, 10 μm) either using 40% ACN in water or 50 ACN in water. After giving either 4 or 5 recycles to get the pure isomer with 19% and 36% yield respectively.

Isomer 25; ¹H NMR (CDCl₃, 400 MHz): δ 7.33-7.28 (m, 4H), 7.26-7.21 (m, 1H), 6.89 (d, J=8.0 Hz, 1H), 6.62 (dd, J=8.0, 2.4 Hz, 1H), 6.58 (d, J=2.8 Hz), 5.38-5.37 (m, 1H), 4.98 (br, 1H), 3.81 (dd, J=6.8, 1.6 Hz, 1H), 3.71 (s, 2H), 2.80-2.76 (m, 2H), 2.62-2.58 (m, 2H), 2.33-2.22 (m, 2H), 2.09-2.00 (m, 2H), 1.89-1.69 (m, 4H), 1.60-1.54 (m, 1H), 1.51-1.41 (m, 2H), 1.07 (s, 3H) ppm; ¹³C NMR (CDCl₃, 100 MHz): δ 154.19, 139.23, 138.40, 136.67, 136.65, 135.35, 130.04, 128.81, 128.48, 126.96, 123.58, 115.67, 113.08, 80.57, 42.15, 39.61, 36.55, 33.21, 32.75, 32.05, 31.90, 31.17, 28.27, 19.90 ppm.

Isomer 26; ¹H NMR (CDCl₃, 400 MHz): δ 7.33 (m, 4H), 7.26-7.21 (m, 1H), 6.89 (d, J=8.0 Hz), 6.62 (dd, J=8.0, 2.8 Hz, 1H), 6.59 (d, J=2.4 Hz, 1H), 5.46-5.45 (m, 1H), 5.21 (brs, 1H), 3.91 (dd J=5.2, 5.2, 1H), 3.71 (s, 2H), 2.80-2.71 (m, 2H), 2.62-2.56 (m, 2H), 2.33-2.28 (m, 1H), 2.25-2.04 (m, 4H), 1.66-1.51 (m, 3H), 1.45-1.30 (m, 2H), 1.03 (s, 3H) ppm; ¹³C NMR (CDCl₃, 100 MHz): δ 154.32, 139.13, 138.38, 136.49, 135.20, 130.00, 129.88, 128.80, 128.50, 126.95, 115.75, 113.09, 79.13, 43.82, 42.34, 36.57, 33.36, 32.74, 32.10, 30.18, 28.99, 21.91, 19.38 ppm.

Example 8

Comparison of CH₃ vs F at Position 5

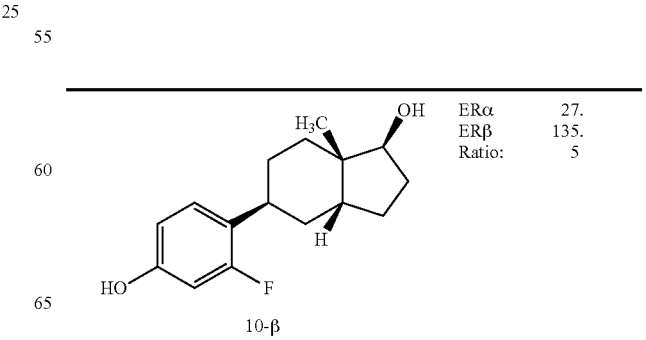

| | |
|---|---|
| ERα | 27. |
| ERβ | 135. |
| Ratio: | 5 |

10-β

-continued

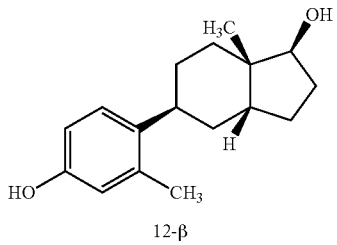 [SMILES: Cc1cc(O)ccc1[C@H]1CC[C@@]2(C)[C@H](CC[C@@H]2O)C1]

12-β

| | | |
|---|---|---|
| ERα | 7.7 | |
| ERβ | 52.8 | |
| Ratio: | 6.9 | |

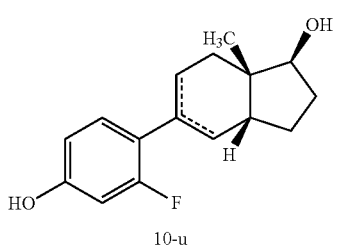

10-u

| | | |
|---|---|---|
| ERa | 4.5 | |
| ERb | 49 | |
| Ratio: | 10.8 | |

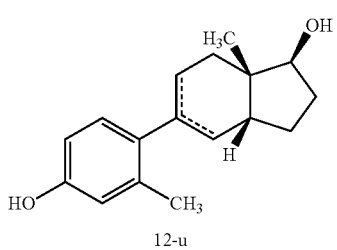

12-u

| | | |
|---|---|---|
| ERα | 4.2 | |
| ERβ | 46.8 | |
| Ratio: | 11.1 | |

Replacement of the 5-H by either $CH_3$ or F leads to rather comparable results. In the natural saturated series the fluoro compounds binds better by a factor of about 2.5; there is almost no difference in the unsaturated series.

Interestingly, the β/α ratio in both series is virtually identical. This suggests that either a methyl group or a fluorine substituent can be used in this position in combination with a substituent at C4 and possibly also at C2.

Example 9

Relative Binding Assays (RBAs)

1. Ring C Saturated Compounds Having the Natural Stereochemistry at C9

Relative binding affinities (RBAs) of a variety of ring A analogs were determined using the method of Kuiper [31]. The RBAs are given with reference to estradiol=100 for both the estrogen alpha and estrogen beta receptor.

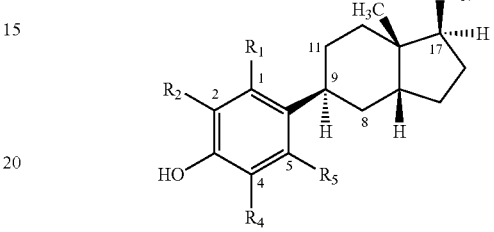

| Entry | $R_1$ | $R_2$ | $R_4$ | $R_5$ | $R_{17}$ | RBAα | RBAβ | RBAβ/RBAα |
|---|---|---|---|---|---|---|---|---|
| | Estradiol | | | | | 100 | 100 | 1 |
| 1. | H | H | H | H | H | 1.5 | 21.5 | 14.6 |
| 2. | H | H | F | H | H | 1.0 | 8.7 | 8.7 |
| 3. | H | H | H | F | H | 27.3 | 135.5 | 5.0 |
| 4. | H | F | F | H | H | 0.4 | 0.28 | 7.0 |
| 5. | H | H | F | F | H | 4.6 | 42.8 | 9.3 |
| 6. | H | F | H | F | H | — | — | — |
| 7. | H | F | F | F | H | 0.19 | 1.73 | 9.1 |
| 8. | H | H | H | Cl | H | 55.3 | 168 | 3.2 |
| 9. | H | H | H | $CH_3$ | H | 2.8 | 33.6 | 11.9 |
| 10. | H | H | H | H | $C_2H$ | 0.09 | 0.11 | 1.2 |

Substituents in the 4 position consistently lowered the binding affinity. This was not unexpected since the both ER receptors have little space to accommodate substituents at this position. Thus for the small F-atom at C4 (entry 2) in comparison to an H at C4 (entry 1), the RBA for ERβ decreased from 21.5% to 8% while the RBA for ERa dropped from 1.7% to 1.0%. This loss in binding affinity by a factor of 2-3

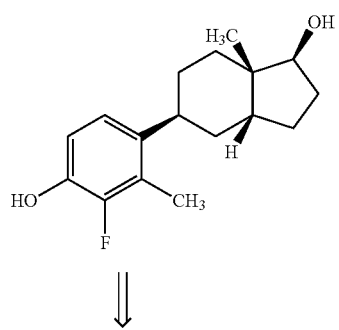

is predicted to show binding similar to

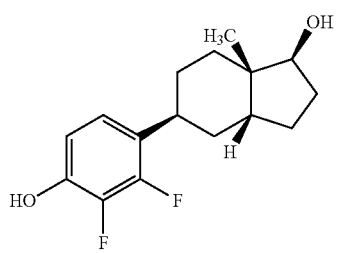

⇓

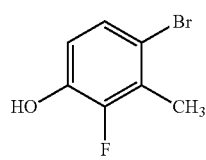

⇓

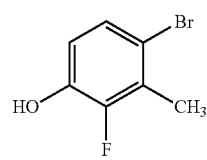

appeared to be amplified in the hormonal potency, where now entry 2 was found to be a weak agonist for ERβ. Fluorine substituents at both positions 2 and 4, as in entry 7, resulted in a further reduction in binding by a factor of about 10 (in comparison with entry 3). The RBAs for the 4-methyl derivative were not measured since those for the precursor unsaturated compounds, entry 21, were already very low [0.5 and 0.02 for ERα and ERβ, respectively].

The docking studies showed that there was some room around C5, which in estradiol connected the saturated B-ring. The RBA studies confirmed that substituents at C5 led to a very high level of activity; i.e., this position is strongly activating. Three derivatives of this type have been synthesized and assayed, entries 3, 8 and 9. The RBA was higher than that found for the parent compound entry 1 irrespective of the type of substituent and, in some cases, exceeded that of estradiol itself for the ERβ receptor (entries 3 and 8, with F or Cl substituents). Interestingly, an increase in the ERβ binding affinity beyond that of estradiol is accompanied by a disproportionately larger increase in ERα and thus a substantially lower binding selectivity. The available transcription activation data followed the same trend.

2. Structures with a Double Bond in Ring C Either C9-C11 or C9-C8

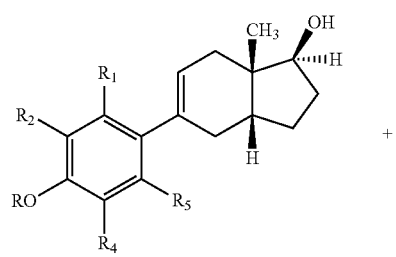

5

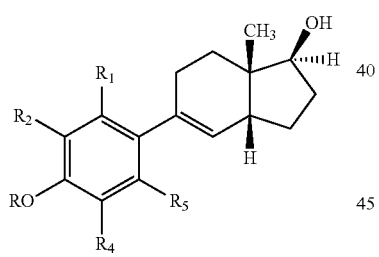

6

The compounds were tested as mixtures except as noted below for entries 16, 17, 19, 20, 25 and 26 in which the separated compounds were tested (as noted)

| Entry | $R_1$ | $R_2$ | $R_4$ | $R_5$ | RBAα | RBAβ | RBAβ/RBAα |
|---|---|---|---|---|---|---|---|
| Estradiol | | | | | 100 | 100 | 1 |
| 11. | H | H | H | H | 0.21 | 2.0 | 9.5 |
| 12. | H | H | F | H | 0.04 | 0.84 | 21 |
| 13. | H | H | H | F | 4.5 | 49 | 10.9 |
| 14. | H | F | F | H | 0.012 | 0.020 | 1.7 |
| 15. | H | H | F | F | 0.78 | 6.8 | 8.7 |
| 16. (5) | H | F | H | F | 0.44 | 2.6 | 5.1 |
| 17. (6) | H | F | H | F | 0.38 | 3.3 | 6.8 |
| 18. | H | F | F | F | 0.19 | 1.73 | 9.1 |
| 19. (5) | H | H | H | Cl | 60 | 118 | 2.0 |
| 20. (6) | H | H | H | Cl | 195 | 331 | 1.7 |
| 21. | H | H | $CH_3$ | H | 0.46 | 0.022 | 0.5 |
| 22. | H | H | H | $CH_3$ | 7.7 | 52.8 | 6.9 |
| 23. | $CH_3$ | H | H | $CH_3$ | 0.5 | 1.1 | 2.2 |
| 24. | H | H | H | $CH=CH_2$ | 0.24 | 3.3 | 13.8 |
| 25. (5) | H | H | H | $CH_2CH_2SCH_2Ph$ | 0.32 | 0.76 | 2.2 |
| 26. (6) | H | H | H | $CH_2CH_2SCH_2Ph$ | 0.31 | 0.27 | 0.86 |

3. ACD Compounds with a 9-Hydroxy Substituent and Having the Natural Stereochemistry at C9.

Most of these compounds have low binding relative to estradiol; however, the compound with a 5-F ring A substituent binds significantly and shows strong beta selectivity. 9-Hydroxy compounds with the un-natural conformation generally have lower binding affinities than those having the natural stereochemistry.

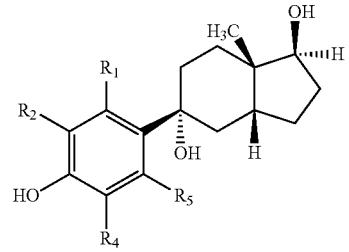

| Entry | $R_1$ | $R_2$ | $R_4$ | $R_5$ | RBAα | RBAβ | RBAβ/RBAα |
|---|---|---|---|---|---|---|---|
| 27. | H | H | H | H | 0.01 | 0.1 | 10 |
| 28. | H | F | H | H | 0.009 | 0.12 | 13 |
| 29. | H | H | H | F | 0.17 | 3.6 | 21 |
| 30. | H | F | F | H | 0.005 | 0.023 | 4.6 |

4. Ring C Saturated Compounds with the Non-Natural Stereochemistry at C9.

Several analogs have been tested. In most cases the binding affinity relative to the compound with the natural stereochemistry at this position is quite low. Several examples are shown to illustrate this point. These compounds appear to be of limited value as estrogen receptor agonists or antagonists.

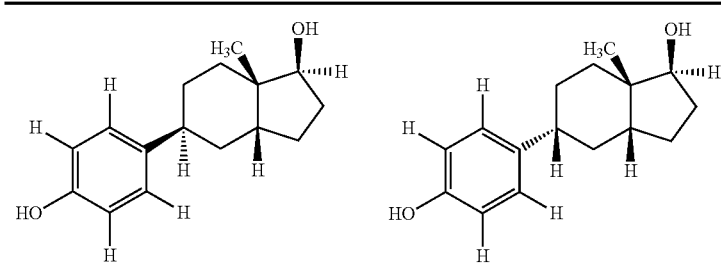
Entry 1
| | | | |
|---|---|---|---|
| RBβ: | 21.5 | RBβ: | 0.61 |
| RBβ/RBα | 14.6 | RBβ/RBα | 10 |
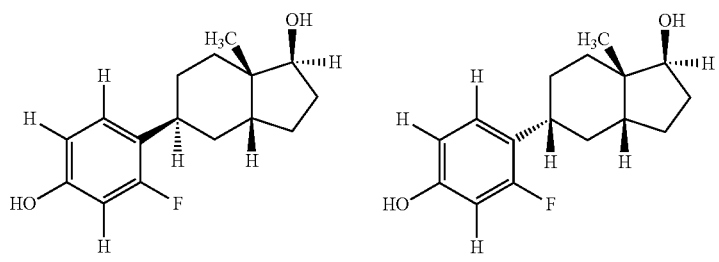
Entry 3
| | | | |
|---|---|---|---|
| RBβ: | 135 | RBβ: | 0.56 |
| RBβ/RBα | 5.0 | RBβ/RBα | 14 |
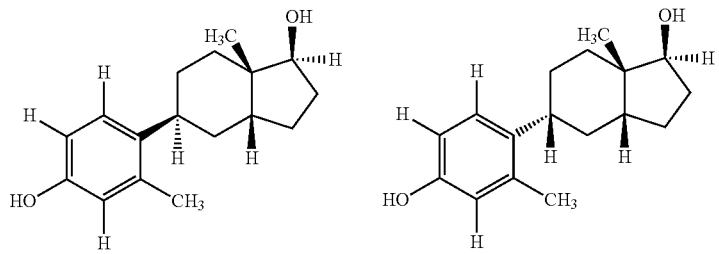
Entry 9
| | | | |
|---|---|---|---|
| RBβ: | 33.6 | RBβ: | 0.055 |
| RBβ/RBα | 11.9 | RBβ/RBα | 0.3 |
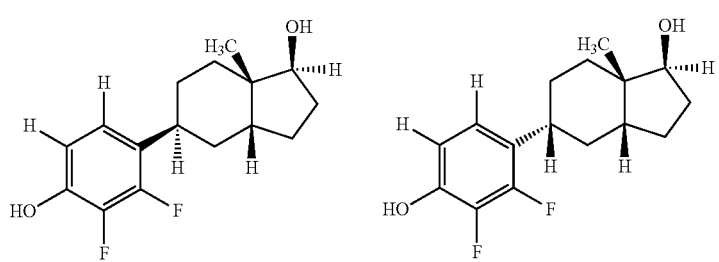
Entry 5
| | | | |
|---|---|---|---|
| RBβ: | 42.8 | RBβ: | 0.15 |
| RBβ/RBα | 9.3 | RBβ/RBα | 0.2 |

Example 10

Comparison of Three 5-F Analogs

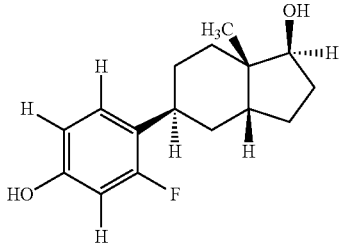 [SMILES: C[C@]12CC[C@H](c3ccc(O)cc3F)C[C@H]1CC[C@@H]2O]

Entry 3

| RBβ: | 135 |
|---|---|
| RBβ/RBα | 5.0 |

Entry 13

| RBβ: | 49 |
|---|---|
| RBβ/RBα | 11 |

Entry 29

| RBβ: | 3.6 |
|---|---|
| RBβ/RBα | 21 |

A substantial decrease [37-fold] in the binding affinity was observed in going from the saturated compound, Entry 3 to the 9-hydroxy compound, Entry 29. It should be noted however that the binding activity of this 9-hydroxy compound is still substantial and that the beta selectivity is as high as of any of the ACD compounds tested thus far. Based on these results, the analagous 5-chloro-9-hydroxy compound is expected to show binding affinity and selectivity comparable to or better than the 5-fluoro analog.

Similar comparisons of the other available 9-hydroxy derivatives showed binding decreases ranging up to 200 fold compared to the saturated analogs.

Example 11

Relative Transcription Assays

The relative transcription activities (RTAs) for a variety of ring analogs were determined [35]. The RTAs are provided below with reference to estradiol=100 for both the estrogen alpha and estrogen beta receptor. Estradiol shows essentially no selectivity for these two receptors.

| Entry | R1 | R2 | R4 | R5 | RTAα | RTAβ | Ratio RTAβ/RTAα |
|---|---|---|---|---|---|---|---|
| Estradiol | | | | | 100 | 100 | 1 |
| 1. | H | H | H | H | 4.3 | 164 | 38 |
| 1* | H | H | H | H [unnatural isomer] | −8.9 | 7.7 | NA |
| 2. | H | H | F | H | −8.3 | 14 | NA |
| 3. | H | H | H | F | 44 | 162 | 3.6 |
| 5. | H | H | F | F | 18 | 151 | 8.4 |
| 7. | H | F | F | F | 11 | 53 | 4.8 |
| 8. | H | H | H | Cl | 88 | 188 | 2.1 |
| 9. | H | H | H | $CH_3$ | −9.7 | 149 | NA |
| 19. | H | H | H | Cl | 120 | 157 | 1.6 |
| 20. | H | H | H | Cl | 98 | 188 | 2.1 |
| 26. | H | H | H | $CH_2CH_2SCH_2Ph$ | 6.7 | 15.6 | 2.2 |

The transcriptional activation of the 5-F derivative, entry 3, shows that this compound, and presumably also the 5-Cl compound, is both an ERα and an ERβ agonist. This behaviour is in contrast to that of the typical SERMs reported in the literature, which are generally either alpha or beta agonists, but not both. The conversion of meta-halogenated phenols into catechols and eventually ortho-quinones has been studied from using computer modelling calculations and have shown that that the formation of these carcinogenic intermediates is significantly slower for the halogenated compounds than from 4-methylphenol itself. Thus these compounds have considerable potential in the field of hormone replacement therapy.

Example 12

Quinone Related Toxicity Assays

The toxicity of selected compounds on intact hepatocytes were measured as LC50 values after 2 hour exposure. The LC50 values represent the concentration (in micromolar units) which caused the death of 50% of the hepatocytes in the sample population. In the present case, the toxicity levels are thought to be correlated with the amount of quinone formed (P. O'Brien, personal communication). The results are shown below. The data confirms that the fully substituted phenol of compound 7 results in decrease of toxicity, perhaps to a baseline level. Compound 7 is the 2,4,5-trifluoro A-CD system, where both ortho positions have been blocked. Of the compounds tested, it shows the lowest toxicity (LC50>600 micromolar). These measurements were conducted at Prof. Peter O'Brien's lab at the Department of Pharmacology, University of Toronto.

Hepatotoxicity of Selected A-CD Compounds

| Entry | LC50 µM |
|---|---|
| Estradiol | 400-450 |
| 1 | 320-400 |
| 2 | 400-450 |
| 3 | 250-280 |
| 5 | 155-200 |
| 7 | >600 |

These data suggest that in order to prevent ortho-hyroxylation and subsequent quinone formation, blocking of the ortho-positions, for example, using F atoms, will form an important part of the design strategy. Compounds whose toxicities approach the high micromolar or millimolar range should be useful as drugs, since the dosage should be in the sub-micromolar range, thus affording a considerable safety factor in usage.

REFERENCES

1. Writing Group for the Women's Health Initiative Investigators, "Risks and benefits of estrogen plus progestin in healthy postmenopausal women: principal results from the Women's Health Initiative randomized controlled trial." *JAMA* 288:321-3 (2002).
2. Rowan T. Chlebowski; Susan L. Hendrix, Robert D. Langer, Marcia L. Stefanick, Margery Gass, Dorothy Lane, Rebecca J. Rodabough, Mary Ann Gilligan, Michele G. Cyr, Cynthia A. Thomson, Janardan Khandekar, Helen Petrovitch, Anne McTiernan, for the WHI Investigators, "Influence of Estrogen Plus Progestin on Breast Cancer and Mammography in Healthy Postmenopausal Women" *JAMA*. 289:3243-3253 (2003).
3. Bernstein, L. The risk of breast, endometrial and ovarian cancer in users of hormonal preparations. MiniReview. *Basic & Clinical Pharmacology & Toxicology* 98, 288-296 (2006).
4. [Parkin, 1997] 4. Parkin, D. M., Whelan, S. L., Ferlay, J., Raymond, L. Young, J. editors. Cancer incidence in five continents. Oxford University Press, 1997.
5. Ruggiero, R. J. and Likis, F. E. Estrogen: Physiology, pharmacology, and formulations for replacement therapy, *J. Midwifery & Women's Health* 47, 130-138 (2002).
6. Wathen, C. N., Feig, D. S., Feightner, J. W., Abramson, B. L. Cheung, A. M. and the Canadian Task Force on Preventive Health Care, "Hormone replacement therapy for the primary prevention of chronic diseases: recommendation statement from the Canadian Task Force on Preventive Health Care", *Canadian Medical Assoc. J.* 170 (2004).
7. Kahlenborn, C. Breast Cancer, Its Link to Abortion and the Birth Control Pill. One More Soul, 2000.
8. Cavalieri, Ercole; Chakravarti, Dhubajyoti; Guttenplan, Joseph; Hart, Elizabeth; Ingle, James; Jankowiak, Ryszard; Muti, Paola; Rogan, Eleanor; Russo, Jose; Santen, Richard; Sutter, Thomas. Catechol estrogen quinones as initiators of breast and other human *Biophysica Acta, Reviews on Cancer* 1766(1), 63-78 (2006).
9. Sarabia, S. F., Zhu, B. T., Kurosawa, T., Tohma, M. and Liehr, J. G., Mechanism of cytochrome P450-catalyzed aromatic hydroxylation of estrogens, *Chem. Res. Toxicol* 10, 767-771 (1997).
10. Zhang, F., Chen, Y., Pisha, E., Shen, l, Xioong, Y., van Breemen, R. B., and Bolton, J. L., The major metabolite of equilin, 4-hydroxyequilin, autoxidizes to an o-quinone which isomerizes to the potent cytotoxin 4-hydroxyequilenin-o-quinone, *Chem. Res. Toxicol.* 12, 204-213 (1999).
11. Bolton, J. L, Quinoids, quinoids radicals, and phenoxyl radicals from estrogens and antiestrogens: Role in carcinogenesis?, *Toxicology* 177, 55-65 (2002).
12. Liu, Xuemei; Yao, Jiaqin; Pisha, Emily; Yang, Yanan; Hua, Yousheng; van Breemen, Richard B.; Bolton, Judy L. Oxidative DNA Damage Induced by Equine Estrogen Metabolites: Role of Estrogen Receptor. *Chemical Research in Toxicology* 15(4), 512-519 (2002).
13. Liu, X., Zhang, F., Liu, H., Burdette, J. E., Li, Y., Cassia, R. O., Pisha, M, Yao, J., van Breemen, R. B., Swanson, S. M. and Bolton, J. L., Effect of halogenated substituents on the metabolism and estrogenic effects of the equine estrogen, equilenin, *Chem. Res. Toxicol.* 16, 741-749 (2003).
14. Yu, L., Liu, H., Li, W., Zhang, F., Luckie, C., van Breemen, R. B., Thatcher, G. R. J., and Bolton, J. L. Oxidation of raloxifene to potential toxic quinoids: Formation of a di-quinone methide and o-quinones. *Chem. Res. Toxicol.* 17, 879-888 (2004).
15. Cavalieri, E. L.; Rogan, E. G.; Chakravarti, D. Initiation of cancer and other diseases by catechol ortho-quinones: a unifying mechanism. *Cellular and Molecular Life Sciences* (2002), 59(4), 665-681 (2002).
16. Cavalieri, Ercole; Rogan, Eleanor; Chakravarti, Dhrubajyoti. The role of endogenous catechol quinones in the initiation of cancer and neurodegenerative diseases. *Methods in Enzymology* (2004), 382(Quinones and Quinone Enzymes, Part B), 293-319.
17. Zahid, M., Kohli, E., Saeed, M., Rogan E. and Cavalieri, E., The greater reactivity of estradiol-3,4-quinone vs. estradiol-2,3-quinone with DNA in the formation of depurinating adducts: Implications for tumor-initiating activity. *Chem. Res. Toxicol.* 19, 164-172 (2006).
18. Hussain, Helmi H.; Babic, Gordana; Durst, Tony; Wright, James S.; Flueraru, Mihaela; Chichirau, Alexandru; Chepelev, Leonid L. Development of Novel Antioxidants: Design, Synthesis, and Reactivity. *Journal of Organic Chemistry* 68(18), 7023-7032 (2003).
19. Chichirau, Alexandru; Flueraru, Mihaela; Chepelev, Leonid L.; Wright, James S.; Willmore, William G.; Durst, Tony; Hussain, Helmi H.; Charron, Martin. Mechanism of cytotoxicity of catechols and a naphthalenediol in PC12-AC cells: the connection between extracellular autoxidation and molecular electronic structure. *Free Radical Biology & Medicine* 38(3), 344-355 (2005).
20. Flueraru, Mihaela; Chichirau, Alexandru; Chepelev, Leonid L.; Willmore, William G.; Durst, Tony; Charron, Martin; Barclay, L. R. C.; Wright, James S. Cytotoxicity and cytoprotective activity in naphthalenediols depends on their tendency to form naphthoquinones. *Free Radical Biology & Medicine* 39(10), 1368-1377 (2005).
21. Flueraru, Mihaela; So, Remmick; Willmore, William G.; Poulter, Michael O.; Durst, Tony; Charron, Martin; Wright, James S. Cytotoxicity and Cytoprotective Activity of Naphthalenediols in Rat Cortical Neurons. *Chemical Research in Toxicology* 19(9), 1221-1227 (2006).
22. O'Brien, P. J. Molecular mechanisms of quinone cytotoxicity. *Chemico-Biological Interactions* 80(1), 1-41 (1991).
23. Pezzella, A., lista, L., Napolitano, A. and d'Ischia, M., Tyrosinase-catalyzed oxidatiioon of 17beta estradiol: Structure elucidation of the products formed beyond catechol estrogen quinones, *Chem. Res. Toxicol.* 18, 1413-1419 (2005).
24. Samuni, A. M., Chuang, E. Y., Krishna, M. C., Stein, W., DeGraff, W., Russo, A. and Mitchell, J. B. Semiquinone radical intermediate in catecholic estrogen-mediated cytotoxicity and mutagenesis: Chemoprevention strategies with antioxidants. *Proc. Nat. Acad. Sci.* 100, 5390-5395 (2003).
25. Springer, C., Adalsteinsson, H., Young, M. M., Kegelmeyer, P. W. and Roe, D. C. PostDOCK: A structural empirical approach to scoring protein ligand complexes. *J. Med. Chem.* 48, 6821-6831 (2005).
26. Alberts, I. L., Todorov, N. P., and Dean, P. M. Receptor flexibility in de novo ligand design and docking. *J. Med. Chem.* 48, 6585-6596 (2005).
27. Glaxo-Smith-Kline corporate review of docking algorithms, 2005.
28. MOE June 2005.06, Chemical Computing Group Inc., Montreal, Canada.
29. Spartan '02, Wavefunction Inc., Irvine, Calif.
30. Kuiper, G. G. L., Carlsson, B., Grandien, K., Enmark, E., Haggblad, J., Nilsson, S., Gustafsson, J., *Endocrinology,* 138 (1997) 863-870.
31. Kuiper, G. G. J., Lemmen J. G., Carlsson, B., Corton, J. C., Safe, S. H., van der Saag, P. T., van der Burg, B., Gustafsson, J., *Endocrinology,* 139 (1998) 4252-4263.

32. Jordan, V. C., Antiestrogens and Selective estrogen receptor modulators as multifunctional medicines. 2. Clinical considerations and new agents, *J. Med. Chem.* 46, 1081-1111 (2003).
33. De Angelis, M., Stossi, F., Carlson, K. A., Katzenellenbogen, B. S. and Katzenellenbogen, J. A., "Indazole estrogens: Highly selective ligands for the estrogen receptor beta", *J. Med. Chem.* 48, 1132-1144 (2005).
34. Jamie B. Scaglione, Brad D. Manion, Ann Benz, Amanda Taylor, Gregory T. DeKoster, | Nigam P. Rath, Alex S. Evers, Charles F. Zorumski, Steven Mennerick, ☐ and Douglas F. Covey, Neurosteroid Analogues. 11. Alternative Ring System Scaffolds: γ-Aminobutyric Acid Receptor Modulation and Anesthetic Actions of Benz[f]indenes., *J. Med. Chem.* 49, 4595-4605 (2006).
35. M. A. C. Pratt, C. A. Crippen and M. Menard. Spontaneous retinoic acid receptor 2 expression during mesoderm differentiation of P19 murine embryonal carcinoma cells. *Differentiation* 65: 271-279 (2000).
36. Palmieri, C.; Cheng, G. J.; Saji, S.; Zelada-Hedman, M.; Warri, A.; Weihua, Z.; Van Noorden, S.; Wahlstrom, T.; Coombes, R. C.; Warner, M.; Gustafsson, J.-A. *Endocr.-Relat. Cancer* 2002, 9, 1.
37. Dahlman-Wright, K.; Cavailles, V.; Fuqua, S. K.; Jordan, V. C.; Katzenellenbogen, J. A.; Korach, K. S.; Maggi, A.; Muramatsu, M.; Parker, M. G.; Gustafsson, J.-A. *Pharmacological Rev.* 2006, 58, 773.
38. Crabtree, J. S.; Zhang, X.; Peano, B. J.; Zhang, Z.; Winneker, R. C.; Harris, H. A. *J. Steroid Biochem. Mol. Biol.* 2006, 101, 11.
39. Harris, H. A.; Albert, L. M.; Leathurby, Y.; Malamas, M. S.; Mewshaw, R. E.; Miller, C. P.; Kharode, Y. P.; Marzolf, J.; Komm, B. S.; Winneker, R. C. et al. *Endocrinology* 2003, 144, 4241.

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A compound of Formula I, or a pharmaceutically acceptable salt, ester or solvate thereof,

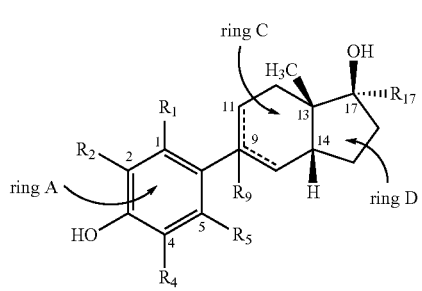

Formula I where
$R_1$ is H, halogen or $CH_3$;
$R_2$ is H, halogen or $CH_3$;
$R_4$ is H, halogen or $CH_3$;
$R_5$ is H, halogen, $CF_3$, $C_1$-$C_5$ alkyl, $CH_2OH$, $CH_2OAc$, $CH_2CH_2OH$, $CH_2CH_2OAc$, $CH_2$-aryl, $CH_2$-heteroaryl, $CH=CH_2$, $CH_2CH_2SCH_3$, $CH_2CH_2SC_2H_5$, $CH_2CH_2SCH_2Ar$, $CH_2CH_2SCH_2$-heteroaryl, OH, $OCH_3$, $OC_2H_5$, $OCH_2Ar$, $OCH_2$-heteroaryl, OAc, $SCH_3$, $SC_2H_5$, $SCH_2Ar$, $SCH_2$-heteroaryl, $SOCH_3$, $SOC_2H_5$, $SOCH_2Ar$, $SOCH_2$-heteroaryl, $SO_2CH_3$, $SO_2C_2H_5$, $SO_2CH_2Ar$, $SO_2CH_2$-heteroaryl, CN, CHO, $COCH_3$, $COC_2H_5$, $CO_2H$, $CO_2CH_3$, $CO_2C_2H_5$, $CO_2CH_2Ar$, $CO_2CH_2$-heteroaryl, $CONH_2$, $CON(CH_3)_2$, $CON(CH_2)_4$, $CON(CH_2)_5$, or $NO_2$;
$R_9$ is absent, H or OH; and
$R_{17}$ is H or $C_2H$.

2. The compound of claim 1 which has the structure of Formula Ia:

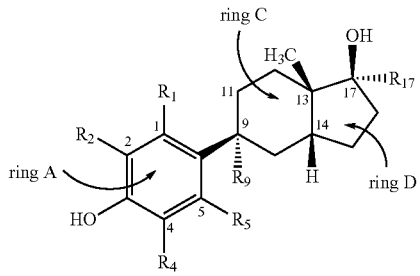

Formula Ia wherein $R_9$ is H or OH.

3. The compound of claim 1, wherein
$R_1$ is H, F or $CH_3$;
$R_2$ is H or F;
$R_4$ is H or F;
$R_5$ is H, F, Cl, $CF_3$, $CH_3$, $C_2H_5$, $nC_3H_7$, $iC_3H_7$, $CH_2OH$, $CH_2OAc$, $CH_2CH_2OH$, $CH_2CH_2OAc$, $CH_2$-aryl, $CH_2$-heteroaryl, $CH=CH_2$, $CH_2CH_2SCH_3$, $CH_2CH_2SC_2H_5$, $CH_2CH_2SCH_2Ar$, $CH_2CH_2SCH_2$-heteroaryl, OH, $OCH_3$, $OC_2H_5$, $OCH_2Ar$, $OCH_2$-heteroaryl, OAc, $SCH_3$, $SC_2H_5$, $SCH_2Ar$, $SCH_2$-heteroaryl, $SOCH_3$, $SOC_2H_5$, $SOCH_2Ar$, $SOCH_2$-heteroaryl, $SO_2CH_3$, $SO_2C_2H_5$, $SO_2CH_2Ar$, $SO_2CH_2$-heteroaryl, CN, CHO, $COCH_3$, $COC_2H_5$, $CO_2H$, $CO_2CH_3$, $CO_2C_2H_5$, $CO_2CH_2Ar$, $CO_2CH_2$-heteroaryl, $CONH_2$, $CON(CH_3)_2$, $CON(CH_2)_4$, $CON(CH_2)_5$ or $NO_2$;
$R_9$=H or OH; and
$R_{17}$ is H or ethynyl.

4. The compound of claim 3, wherein $R_2$ and $R_4$ are H.
5. The compound of claim 3, wherein $R_5$ is H, F, Cl or $CH_3$.
6. The compound of claim 1, wherein said halogen is F or Cl.
7. The compound of claim 1, wherein at least one of $R_1$, $R_2$, $R_4$, and $R_5$ is not H.
8. The compound of claim 3, wherein $R_2$, $R_4$ and $R_5$ are F, and $R_1$, $R_9$ and $R_{17}$ are H.
9. The compound of claim 3, wherein $R_1$, $R_2$, $R_4$, $R_5$, $R_9$ and $R_{17}$ are each H.
10. The compound of claim 2, wherein $R_1$, $R_2$, $R_4$, $R_9$ and $R_{17}$ are each H and $R_5$ is F or Cl.
11. The compound of claim 2, wherein
$R_1$ is H, F or $CH_3$;
$R_2$ is H or F;
$R_4$ is H or F;
$R_5$ is H, F, Cl, $CF_3$, $CH_3$, $C_2H_5$, $nC_3H_7$, $iC_3H_7$, $CH_2OH$, $CH_2OAc$, $CH_2CH_2OH$, $CH_2CH_2OAc$, $CH_2$-aryl, $CH_2$-heteroaryl, $CH=CH_2$, $CH_2CH_2SCH_3$, $CH_2CH_2SC_2H_5$, $CH_2CH_2SCH_2Ar$, $CH_2CH_2SCH_2$-heteroaryl, OH, $OCH_3$, $OC_2H_5$, $OCH_2Ar$, $OCH_2$-heteroaryl, OAc, $SCH_3$, $SC_2H_5$, $SCH_2Ar$, $SCH_2$-heteroaryl, $SOCH_3$, $SOC_2H_5$, $SOCH_2Ar$, $SOCH_2$-heteroaryl, $SO_2CH_3$, $SO_2C_2H_5$, $SO_2CH_2Ar$, $SO_2CH_2$-heteroaryl, CN, CHO, $COCH_3$, $COC_2H_5$, $CO_2H$, $CO_2CH_3$, $CO_2C_2H_5$, $CO_2CH_2Ar$, $CO_2CH_2$-heteroaryl, $CONH_2$, $CON(CH_3)_2$, $CON(CH_2)_4$, $CON(CH_2)_5$ or $NO_2$;

$R_9$ is H or OH; and $R_{17}$ is H or ethynyl.

12. The compound of claim 11, wherein $R_2$ and $R_4$ are H.

13. The compound of claim 11, wherein $R_5$ is H, F, Cl or $CH_3$.

14. The compound of claim 2, wherein said halogen is F or Cl.

15. The compound of claim 2, wherein at least one of $R_1$, $R_2$, $R_4$, and $R_5$ is not H.

16. The compound of claim 11, wherein $R_2$, $R_4$ and $R_5$ are F, and $R_1$, $R_9$ and $R_{17}$ are H.

17. The compound of claim 11, wherein $R_1$, $R_2$, $R_4$, $R_5$, $R_9$ and $R_{17}$ are each H.

\* \* \* \* \*

UNITED STATES PATENT AND TRADEMARK OFFICE
CERTIFICATE OF CORRECTION

PATENT NO. : 8,471,073 B2  
APPLICATION NO. : 13/431201  
DATED : June 25, 2013  
INVENTOR(S) : Hooman Shadnia et al.

Page 1 of 1

It is certified that error appears in the above-identified patent and that said Letters Patent is hereby corrected as shown below:

In the Specification

Column 34 line 41: After "RBA for" delete "ERa" and replace with -- ER$\alpha$ --

Signed and Sealed this  
Thirteenth Day of August, 2013

Teresa Stanek Rea  
*Acting Director of the United States Patent and Trademark Office*